US010769242B2

(12) United States Patent
Aronow et al.

(10) Patent No.: US 10,769,242 B2
(45) Date of Patent: Sep. 8, 2020

(54) SYSTEM AND METHOD FOR DATA MINING VERY LARGE DRUGS AND CLINICAL EFFECTS DATABASES

(71) Applicant: Cincinnati Children's Hospital Medical Center, Cincinnati, OH (US)

(72) Inventors: Bruce Aronow, Cincinnati, OH (US); Mayur Sarangdhar, Cincinnatti, OH (US); Scott Carl Tabar, Hamilton, OH (US); Anil Goud Jegga, West Chester, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 546 days.

(21) Appl. No.: 15/541,435

(22) PCT Filed: Jan. 5, 2016

(86) PCT No.: PCT/US2016/012208
§ 371 (c)(1),
(2) Date: Jul. 3, 2017

(87) PCT Pub. No.: WO2016/112025
PCT Pub. Date: Jul. 14, 2016

(65) Prior Publication Data
US 2018/0004902 A1 Jan. 4, 2018

Related U.S. Application Data

(60) Provisional application No. 62/099,923, filed on Jan. 5, 2015.

(51) Int. Cl.
*G06F 16/00* (2019.01)
*G06F 19/00* (2018.01)
(Continued)

(52) U.S. Cl.
CPC ........ *G06F 19/326* (2013.01); *G06F 16/2465* (2019.01); *G06Q 50/22* (2013.01); *G16H 10/60* (2018.01)

(58) Field of Classification Search
None
See application file for complete search history.

(56) References Cited

U.S. PATENT DOCUMENTS 8,676,608 B2 * 3/2014 Oesterheld .......... G06F 19/3456
705/3
9,135,097 B2 * 9/2015 Sridharan ........... G06F 11/0709
(Continued)

OTHER PUBLICATIONS

International Search Report dated Apr. 8, 2016, issued for International Patent Application PCT/US2016/012208.
(Continued)

*Primary Examiner* — Debbie M Le
(74) *Attorney, Agent, or Firm* — BakerHostetler

(57) ABSTRACT

A current system allows data-driven hypothesis generation to identify therapeutic candidates for a disease phenotype treatment by identifying drugs and clinical indications associated with lower occurrences of disease-associated phenotype(s) by a drug/drug class. A current system may include a pharmaceutical hierarchical ontology; a phenotype hierarchical ontology; a record database comprising clinical event records; a database mining engine; and a mapping engine. The database mining engine may iteratively progress through a portion of the pharmacological hierarchical ontology and phenotype hierarchical ontology to iteratively select pairs of cohort entries from each ontology; and for each pair of cohort entries, query the clinical record database for matching records. The mapping engine may map each pair of cohort entries into a matrix comprising a drug-event cell for each pair and apply a value thereto representing the
(Continued)

number of database records matching items returned by the database mining engine for the corresponding cohort entries.

32 Claims, 35 Drawing Sheets

(51) Int. Cl.
*G06F 16/2458* (2019.01)
*G06Q 50/22* (2018.01)
*G16H 10/60* (2018.01)

(56) References Cited

U.S. PATENT DOCUMENTS

| | | | |
|---|---|---|---|
| 10,664,366 B2* | 5/2020 | Schatz | ................ G06F 11/2033 |
| 2003/0233339 A1 | 12/2003 | Downs | |
| 2006/0028471 A1 | 2/2006 | Kincaid et al. | |
| 2007/0005621 A1* | 1/2007 | Lesh | ....................... G16H 15/00 |
| 2008/0294459 A1* | 11/2008 | Angell | .................. G06F 19/328 |
| | | | 705/2 |
| 2009/0006607 A1 | 1/2009 | Bu et al. | |
| 2011/0184250 A1 | 7/2011 | Schmidt et al. | |
| 2011/0189185 A1 | 8/2011 | Lizard et al. | |
| 2013/0226616 A1 | 4/2013 | Nigam et al. | |
| 2013/0179375 A1 | 7/2013 | Tatonetti et al. | |
| 2014/0222349 A1* | 8/2014 | Higgins | ................. G16B 20/00 |
| | | | 702/19 |
| 2014/0350954 A1* | 11/2014 | Ellis | ....................... G16H 50/20 |
| | | | 705/2 |
| 2018/0276251 A1* | 9/2018 | Srinivasan | ............. G06F 16/27 |

OTHER PUBLICATIONS

International Patent Application No. PCT/US2016/012208; Int'l Preliminary Report on Patentability; dated Jul. 20, 2017; 9 pages.

* cited by examiner

| ISR | Age | AgeCode | Gender | Occp | DrugName | Indications | Reactions |
|---|---|---|---|---|---|---|---|
| 5317993 | 21.0 | YR | F | MD | mifepristone tablets, 200 mg [danco labs]; misoprostal; | abortion induced; | white blood cell count increased;hypodaemic shock anaemia abortion incomplete; |
| 4204616 | 21.0 | YR | F | MD | mifepristone tablets, 200 mg [danco labs]; misoprostal; | abortion induced; | white blood cell count increased;nausea uterine tenderness, abdominal pain;heart rate increased p?? |
| 4493858 | 21.0 | YR | F | OT | mifepristone tablets, 200 mg [danco labs]; misoprostal; | abortion induced; | white blood cell count increased;ad?? uteri pain;uterine enlargement pain;uterine tenderness;drug ?? |
| 4634985 | 20.0 | YR | F | OT | mifepristone tablets, 200 mg [danco labs]; misoprostal; | abortion induced; | white blood cell count increased; haemoglobin decreased;vaginal haemorrhage pain;drug exposure durin |

FIG. 3

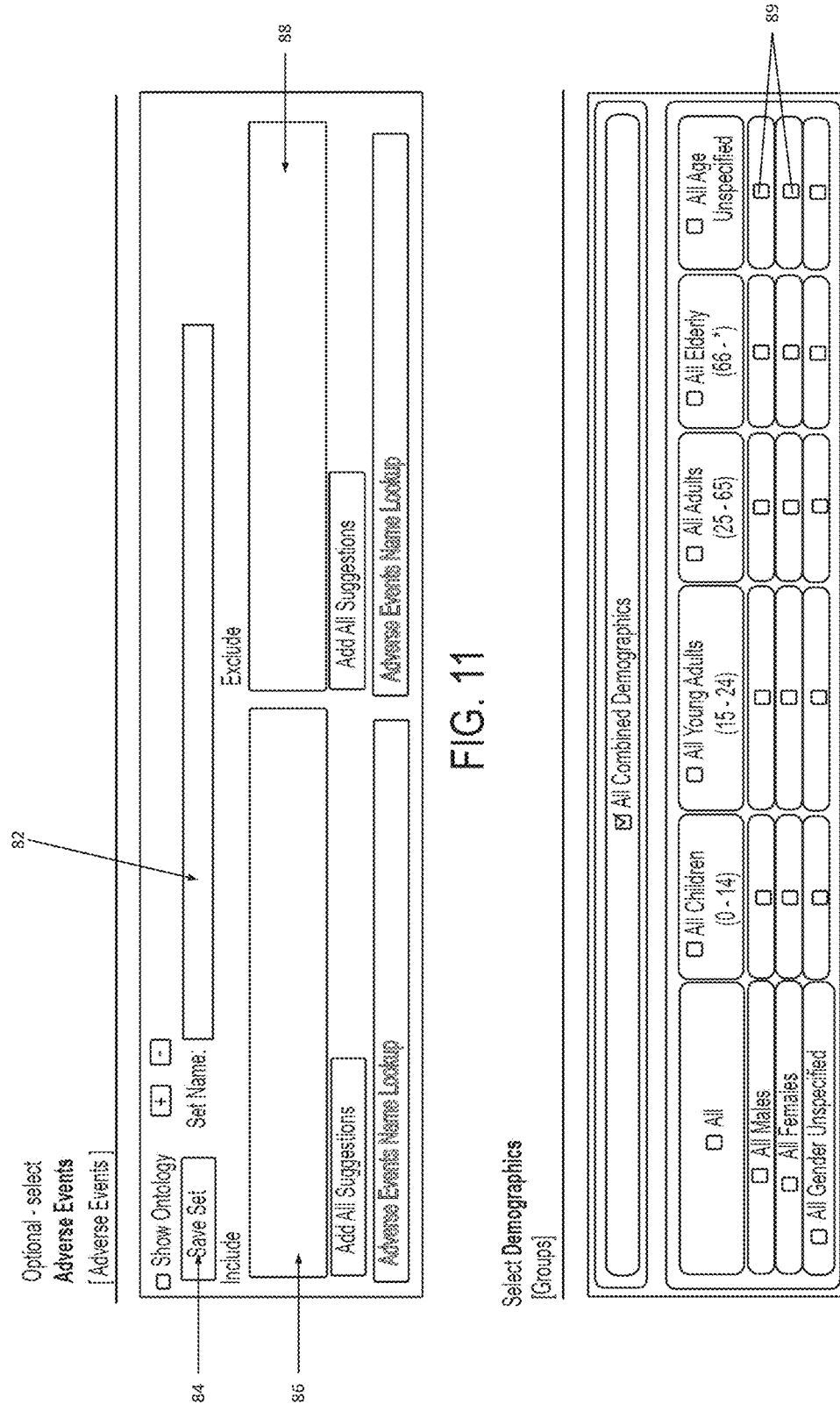

Analysis Filters

| Enable | Filter Type | Filter | | Aggregated Analysis Stats | | |
|---|---|---|---|---|---|---|
| | | | columns per row must match each filter | Min | Max | Rows Included |
| ☑ | Column Filter | ≥ | 3 | 1 | 9 | 5,496 |
| ☑ | Absolute Counts | ≥ | 10.000 | 1 | 25.112 | 867 |
| ☐ | Per 1000 Patients | ≥ | 1.000 | 0.002 | 334.708 | 4,943 |
| ☑ | Relative Risk | ≥ | 2.000 | 0.006 | 833.093 | 6,498 |
| ☑ | Relative Risk pValue | ≤ | 0.050 | 0.000 | 1.000 | 8,861 |
| ☑ | IC | > | 0.000 | -7.249 | infinity | 2,626 |
| | | To apply filters just click on any of the Analysis links within the Analysis Matrix | | Filtered Results: | | |

FIG. 13

| Rank | Adverse Events | Total_Adverse_Events_Reports | Absolute Counts_cardiac therapy_aggregated | Absolute Counts_antihypertensives_aggregated | Absolute Counts_diuretics_aggregated | Absolute Counts_peripheral vasodi..._aggregated | Absolute Counts_vasoprotectives_aggregated | Absolute Counts_beta blocking agents_aggregated | Absolute Counts_calcium channel b..._aggregated | Absolute Counts_agents acting on ..._aggregated | Absolute Counts_lipid modifying a..._aggregated |
|---|---|---|---|---|---|---|---|---|---|---|---|
| | Unique Patients | | 250,325 | 110,056 | 287,705 | 59,640 | 272,319 | 299,954 | 223,713 | 418,226 | 438,816 |
| 1 | angina unstable | 4,724 | 1,165 | 200 | 1,029 | 106 | 778 | 1,380 | 809 | 1,649 | 1,674 |
| 2 | benign prostatic hyperplasia | 2,373 | 475 | 176 | 479 | 38 | 386 | 524 | 412 | 705 | 696 |
| 3 | mononeuropathy | 109 | 8 | | 8 | 14 | 18 | 3 | 13 | 16 | 25 |
| 4 | blood cholesterol | 170 | 25 | 6 | 21 | 1 | 9 | 41 | 26 | 43 | 58 |
| 5 | exposure to chemical pollution | 40 | 9 | 1 | 9 | 6 | 9 | 10 | 7 | 12 | 11 |
| 6 | joint range of motion decreased | 3,266 | 601 | 314 | 537 | 86 | 492 | 749 | 610 | 757 | 720 |
| 7 | gastritis | 12,783 | 2,041 | 587 | 2,028 | 187 | 1,805 | 2,022 | 1,453 | 2,715 | 2,462 |
| 8 | scrotal infection | 72 | 10 | 12 | 6 | 10 | 11 | 5 | 11 | 10 | 19 |
| 9 | synovial rupture | 154 | 37 | 15 | 54 | 2 | 50 | 15 | 5 | 70 | 57 |
| 10 | astigmatism | 534 | 101 | 26 | 71 | 2 | 127 | 98 | 64 | 64 | 75 |
| 11 | essential thrombocythaemia | 146 | 33 | 24 | 58 | 20 | 64 | 58 | 31 | 52 | 40 |

FROM FIG. 14A

| | | | | | | | | | |
|---|---|---|---|---|---|---|---|---|---|
| 12 upper gastrointestinal haemorrhage | 3,392 | 635 | 101 | 632 | 57 | 507 | 594 | 419 | 699 | 596 |
| 13 arteriospasm coronary | 1,379 | 322 | 19 | 117 | 25 | 207 | 185 | 181 | 184 | 173 |
| 14 sinus pain | 84 | 6 | 3 | 8 | | 2 | 4 | 18 | 17 | 22 |
| 15 catheter site haemorrhage | 604 | 111 | 42 | 84 | 5 | 187 | 114 | 61 | 88 | 97 |
| 16 renal lipomatosis | 45 | 28 | 1 | 4 | | 14 | 1 | 3 | 4 | 17 |
| 17 eyelid cyst | 54 | 8 | | 10 | 1 | 3 | 10 | 1 | 7 | 13 |
| 18 cataract cortical | 82 | 21 | 7 | 26 | 8 | 16 | 21 | 15 | 30 | 16 |
| 19 hypertensive crisis | 3,380 | 375 | 390 | 677 | 8 | 337 | 822 | 601 | 1,214 | 418 |
| 20 cerebral atrophy | 2,964 | 577 | 162 | 655 | 55 | 610 | 643 | 488 | 812 | 650 |
| 21 faeces hard | 659 | 85 | 26 | 68 | 19 | 39 | 67 | 83 | 106 | 120 |
| 22 hyperglycaemic hyperosmolar nonketotic syndrome | 246 | 19 | 11 | 37 | 3 | 47 | 24 | 23 | 52 | 43 |
| 23 postmenopausal haemorrhage | 942 | 91 | 24 | 142 | 7 | 140 | 109 | 64 | 176 | 162 |
| 24 presbyopia | 352 | 98 | 17 | 77 | 4 | 94 | 69 | 92 | 120 | 113 |
| 25 hypoglycaemic unconsciousness | 1,008 | 90 | 55 | 137 | 14 | 61 | 144 | 99 | 241 | 227 |

FIG. 14B

Beneficial?? Harmful complications
Adverse Events
-3   0   3

Table - Drug Recommender

| | arbs | beta blockers | calcium ch. Blockers | lipid modifying agts | antithrombotics | vasodilators |
|---|---|---|---|---|---|---|
| mydriasis | -1.12 | -0.375 | -0.779 | -1.178 | -0.746 | 0.187 |
| hyperacusis | -0.474 | -0.608 | -0.634 | -1.122 | -0.918 | 0.038 |
| irritability | -0.61 | -0.356 | -0.705 | -0.104 | -0.65 | -0.096 |
| personality change | -0.819 | -0.22 | -0.245 | -0.023 | -0.415 | -0.105 |
| salivary hypersecretion | -0.824 | -0.414 | -0.271 | -0.074 | -0.682 | -0.162 |
| abnormal behaviour | -0.876 | -0.585 | -0.722 | -0.653 | -0.916 | -0.064 |
| schizophrenia | -1.067 | -0.578 | -0.534 | -0.606 | -1.155 | -0.112 |
| mood altered | -0.907 | -0.356 | -0.376 | -0.262 | -1.027 | 0.124 |
| anger | -1.183 | -0.46 | -0.951 | -0.195 | -1.107 | -0.193 |
| bipolar disorder | -0.946 | -0.285 | -0.661 | -0.144 | -1.116 | -0.386 |
| panic reaction | -0.224 | -0.142 | -0.463 | -0.222 | -1.16 | -0.467 |
| nystagmus | -0.772 | -0.232 | -0.438 | -0.277 | -0.305 | -1.445 |
| paranoia | -1.023 | -0.379 | -0.64 | -0.248 | -0.738 | -0.846 |
| thinking abnormal | -0.734 | -0.328 | -0.699 | -0.221 | -0.501 | -0.629 |
| drug level decreased | -1.001 | -0.135 | -0.148 | -0.116 | -0.281 | -0.47 |
| affect lability | -1.169 | -0.696 | -0.864 | -0.842 | -1.5 | -0.98 |
| suicidal ideation | -1.062 | -0.702 | -0.993 | -0.576 | -1.363 | -0.901 |
| aggression | -1.211 | -0.666 | -0.967 | -0.64 | -0.908 | -0.508 |
| psychotic disorder | -1.346 | -0.486 | -0.903 | -0.601 | -1.011 | -0.943 |
| logorrhoea | -0.661 | -0.641 | -0.88 | -0.566 | -0.984 | -1.53 |
| mania | -0.684 | -0.793 | -0.858 | -0.396 | -1.216 | -1.067 |
| antipsychotic drug level increased | -1.242 | -0.951 | -0.954 | -0.185 | -0.709 | -1.168 |
| suicidal behaviour | -1.013 | -0.688 | -1.935 | -0.585 | -0.718 | -0.762 |
| completed suicide | -1.374 | -0.124 | -0.037 | -1.255 | -1.741 | -1.159 |
| multiple drug overdose intentional | -1.374 | -0.049 | 0.029 | -1.339 | -1.596 | -0.725 |
| suicide attempt | -1.134 | -0.683 | -0.424 | -1.207 | -1.604 | -1.018 |
| poisoning | -0.885 | 0.111 | -0.18 | -0.989 | -1.344 | -0.673 |
| therapeutic response unexpected with drug substitution | -1.613 | -0.212 | -0.468 | -1.403 | -2.104 | -1.584 |

FIG. 20

Relative Risks

| | Reactions | Total Occurrences | acetaminophen \| All | ibuprofen \| All | Rx-acetaminophen \| All | Rx-ibuprofen \| All |
|---|---|---|---|---|---|---|
| ☑ | headache | 136326 | 8946  a | 3936 | 132287  c | 133892 |
| ☑ | sinus headache | 2241 | 134 | 90 | 2190 | 2173 |
| ☑ | tension headache | 942 | 95 | 46 | 886 | 909 |
| ☑ | cluster headache | 331 | 46 | 15 | 325 | 322 |
| ☑ | drug withdrawal headache | 123 | 17 | 2 | 118 | 121 |
| ☑ | post-traumatic headache | 56 | 7 | 7 | 52 | 50 | Control set for acetaminophen |
| ☑ | procedural headache | 65 | 5 | 1 | 65 | 64 | Control set for ibuprofen |
| ☑ | postictal headache | 33 | 5  b | | | 32  d | 33 |
| ☑ | post procedural headache | 3 | 2 | | 3 | 3 |
| ☑ | headache postoperative | 11 | 1 | 1 | 11 | 11 |
| ☑ | exertional headache | 7 | 1 | | 6 | 7 |
| ☑ | lumbar puncture headache | 31 | 1 | 3 | 31 | 28 |
| ☑ | cervicogenic headache | 16 | 1 | | 15 | 15 |
| ☑ | cold-stimulus headache | 8 | | | 8 | 8 |
| ☑ | vascular headache | 56 | | 3 | 56 | 56 |
| UniqueCount | | | 176084  a+b | 65832 | 4041759  c+d | 4100748 |

| | | Reactions | |
|---|---|---|---|
| | | + | − |
| | Exposed | a | b |
| | Not Exposed | c | d |

$$RR = \left(\frac{a}{a+b}\right) \Big/ \left(\frac{c}{c+d}\right)$$

FIG. 21

Information Component (IC)

| | Reactions | Total Occurrences | acetaminophen \| All | ibuprofen \| All | Rx-acetaminophen \| All | Rx-ibuprofen \| All |
|---|---|---|---|---|---|---|
| ☑ | | | AE_count | | | |
| ☑ | headache | 136326 AE Total | 8946 | 3936 | 132287 | 133892 |
| ☑ | sinus headache | 2241 | 134 | 90 | 2190 | 2173 |
| ☑ | tension headache | 942 | 96 | 46 | 886 | 909 |
| ☑ | cluster headache | 331 | 46 | 15 | 325 | 322 |
| ☑ | drug withdrawal headache | 123 | 17 | 2 | 118 | 121 |
| ☑ | post-traumatic headache | 56 | 7 | 7 | 52 Control set for | 50 Control set for |
| ☑ | procedural headache | 65 | 5 | 1 | 65 acetaminophen | 64 ibuprofen |
| ☑ | postictal headache | 33 | 5 | | 32 | 33 |
| ☑ | post procedural headache | 3 | 2 | | 3 All other drugs | 3 All other drugs |
| ☑ | headache postoperative | 11 | 1 | 1 | 11 NO | 11 NO |
| ☑ | exertional headache | 7 | 1 | | 6 acetaminophen | 7 ibuprofen |
| ☑ | lumbar puncture headache | 31 | 1 | 3 | 31 | 28 |
| ☑ | cervicogenic headache | 16 | 1 | | 15 | 16 |
| ☑ | cold-stimulus headache | 8 | | | 8 | 8 |
| ☑ | vascular headache | 56 | | 3 | 56 | 56 |
| UniqueCount | UniquePatients | → 176084 | | 65832 | 4041759 | 4100748 |

IC(AE) = log2((AE_count*T)/(UniquePatients*AE Total));

T = total number of reports (unduplicated)

FIG. 22

Example of generating mutually exclusive sets - ACE inhibitors vs ARBs (angiotensin ii receptor antagonists) vs diuretics as a function of demographics (adult, elderly, males, females) within Indication-anchored patient subsets

Analysis: rich, high content data

| Rank Adverse Events | Total_ Adverse Events_ Reports | Relative Risk_ ace inhibitors, p_ adults male | Relative Risk_ angiotensin i an_ adults male | Relative Risk_ diuretics_ adults male | Relative Risk_ ace inhibitors, p_ elderly males |
|---|---|---|---|---|---|
| Unique Patients | | 28,534 | 15,115 | 16,375 | 25,051 |
| 1 hepatic function abnormal | 15,981 | 0.156 | 2.776 | 1.936 | 0.245 |
| 2 gingival infection | 1,828 | 0.250 | 0.734 | 3.491 | 1.881 |
| 3 blood pressure inadequately controlled | 3,763 | 0.437 | 3.240 | 0.366 | 0.621 |
| 4 oral pain | 6,724 | 0.564 | 0.182 | 3.969 | 0.749 |
| 5 peripheral embolism | 633 | 1.522 | 0.422 | 1.496 | 0.091 |
| 6 nasal disorder | 670 | 1.803 | 0.843 | 0.457 | 1.568 |
| 7 erysipelas | 1,480 | 0.451 | 0.888 | 2.841 | 0.513 |
| 8 tooth infection | 3,749 | 0.842 | 0.747 | 1.302 | 0.672 |
| 9 aortic dilatation | 535 | 1.028 | 0.723 | 1.422 | 0.557 |
| 10 right ventricular systoic pressure increased | 152 | 0.902 | | 4.115 | 1.045 |
| 11 duodental ulcer haemorrhage | 1,230 | 0.528 | 3.917 | 0.338 | 0.671 |
| 12 kyphoscoliosis | 267 | | | | |
| 13 artariovenous malformation | 396 | 2.164 | 0.318 | 0.914 | 0.182 |
| 14 effusion | 644 | 0.464 | 0.465 | 4.267 | 0.697 |
| 15 anaemia haemolytic autoimmune | 1,283 | 0.676 | 0.949 | 1.829 | 2.299 |
| 16 peripheral vascular disorder | 3,698 | 1.178 | 0.407 | 1.352 | 0.496 |
| 17 post-traumatic stress disorder | 1,974 | 2.282 | 0.067 | 1.324 | 2.090 |
| 18 life expectancy shortened | 1,028 | 4.959 | 0.126 | 0.490 | 0.322 |
| 19 granuloma | 1,753 | 0.902 | 0.206 | 2.110 | 1.344 |
| 20 dental garies | 8,023 | 0.585 | 0.408 | 2.961 | 4.041 |
| 21 presbyopia | 352 | 29.754 | 0.100 | | 0.261 |
| 22 pain in jaw | 11,529 | 0.858 | 0.275 | 2.368 | 0.896 |
| 23 metastases to lymph nodes | 2,248 | 1.074 | 0.455 | 1.114 | 0.577 |
| 24 purulent discharge | 2,699 | 0.889 | 0.295 | 1.588 | 0.976 |
| 25 cerebellar syndrome | 1,019 | 0.507 | 0.190 | 5.290 | 1.844 |
| 26 epiglottic oedema | 120 | 18.258 | 0.271 | | |
| 27 primary sequestrum | 2,891 | 0.644 | 0.542 | 1.905 | 0.906 |
| 28 lip dry | 2,793 | 2.198 | 0.949 | 0.161 | 2.090 |
| 29 stress fracture | 3,897 | 0.783 | 0.422 | 3.135 | |
| 30 urine odour abnormal | 1,403 | 0.878 | 2.277 | 0.588 | 0.880 |

TO FIG. 23B

Sample demonstration: Differential risk across of ace inhibitors vs arbs vs diuretics <= 1: Negligible or minimal risk (under-representation/inverse correlation)
>1 <=2: Moderate risk
>2: High risk

FIG. 23A

FROM FIG. 23A

| Relative Risk_ angiotensin ii an..._ elderly males | Relative Risk_ diuretics_ elderly males | Relative Risk_ace inhibitors, p..._ adult females | Relative Risk_ angiotensin ii an..._ adult females | Relative Risk_ diuretics_ adult females | Relative Risk_ace inhibitors, p..._ elderly females | Relative Risk_ angiotensin ii an..._ elderly females | Relative Risk_ diuretics_ elderly females |
|---|---|---|---|---|---|---|---|
| 17,679 | 22,974 | 24,797 | 17,181 | 28,381 | 23,972 | 24,895 | 32,510 |
| 3.042 | 1.259 | 0.305 | 2.688 | 1.191 | 0.270 | 2.348 | 1.238 |
| 0.364 | 0.955 | 0.731 | 0.498 | 1.689 | 2.799 | 0.574 | 0.632 |
| 2.377 | 0.451 | 0.369 | 3.575 | 0.316 | 0.638 | 2.486 | 0.470 |
| 0.571 | 1.506 | 1.620 | 0.347 | 1.208 | 0.888 | 0.591 | 1.982 |
| 0.133 | 16.234 | 1.060 | 1.108 | 1.084 | 1.760 | 0.553 | 1.307 |
| 0.218 | 1.910 | 1.074 | 0.097 | 2.601 | 0.210 | 0.468 | 6.136 |
| 0.692 | 2.387 | 0.744 | 1.361 | 0.782 | 0.846 | 0.803 | 0.912 |
| 0.449 | 2.896 | 1.835 | 0.554 | 0.883 | 1.641 | 0.802 | 0.841 |
| 0.362 | 2.965 | 0.892 | 1.410 | 1.012 | 0.989 | 0.507 | 1.753 |
|  | 3.820 | 5.131 |  | 0.680 | 1.181 |  | 3.579 |
| 0.752 | 1.864 | 1.201 | 1.212 | 0.865 | 0.710 | 0.578 | 1.732 |
|  |  |  |  |  | 0.332 |  | 13.039 |
| 4.178 | 0.191 | 0.992 | 1.939 | 0.303 | 2.250 | 0.488 | 0.153 |
| 0.675 | 1.337 | 0.686 | 0.554 | 1.180 | 0.787 | 0.870 | 0.767 |
| 0.640 | 0.273 | 0.172 | 0.298 | 3.685 | 0.977 | 0.369 | 1.888 |
| 0.373 | 3.251 | 1.032 | 0.579 | 1.046 | 1.186 | 0.408 | 1.196 |
| 1.426 | 0.409 | 0.972 | 0.301 | 1.956 | 1.575 | 0.277 | 0.511 |
| 0.095 | 7.639 | 0.120 | 0.456 | 3.968 | 1.856 | 0.861 | 0.297 |
| 0.133 | 1.910 | 0.397 | 0.712 | 1.979 | 0.525 | 1.217 | 1.087 |
| 0.201 | 0.646 | 0.911 | 0.614 | 1.501 | 0.924 | 0.380 | 2.301 |
|  | 15.279 | 1.544 | 0.323 | 0.828 | 1.575 |  | 1.726 |
| 0.526 | 1.574 | 0.803 | 0.489 | 1.846 | 1.323 | 0.571 | 1.398 |
| 1.529 | 0.716 | 0.713 | 0.901 | 1.301 | 0.054 | 0.461 | 2.337 |
| 0.446 | 1.846 | 0.450 | 0.474 | 2.428 | 1.496 | 0.130 | 1.442 |
| 0.788 | 0.260 | 0.744 | 1.193 | 1.012 | 0.225 | 0.543 | 3.287 |
| 0.272 | 0.637 | 0.301 | 0.351 | 3.282 | 0.822 | 0.044 | 4.362 |
| 1.143 | 0.174 | 0.149 | 0.462 | 7.017 | 0.859 | 2.787 | 0.264 |
| 1.657 | 1.910 | 0.379 | 0.810 | 1.583 | 1.369 | 0.595 | 1.096 |
| 3.153 | 0.503 | 1.846 | 0.578 | 0.700 | 0.360 | 1.127 | 1.797 |

Solr Query Run Times Ms (Total 1,664 ms)
Unique Patients

| | | | 87 ms | 62 ms | 114 ms | 62 ms | 70 ms | 62 ms | 78 ms | 62 ms |
|---|---|---|---|---|---|---|---|---|---|---|
| | | | 77,360 | 2929 | 77,360 | 2,329 | 21,729 | 2,134 | 21,729 | 2,134 |

| | | | | Absolute Count | Absolute Count/Omega iC/Omega | Absolute Count | Absolute Count/Omega iC/Omega | Absolute Count | Absolute Count/Omega iC/Omega |
|---|---|---|---|---|---|---|---|---|---|

| Rank | Adverse Event Adverse Events | Code | Count | Total_Adverse | apsy-noARBs adult females | apsy-ARBs adult females | Absolute Count/Absolute Count/Omega api iC/Omega_apip-values | apsy-noARBs adult females | apsy-ARBs adult females p-values | apsy-noARBs elderly females | apsy-ARBs elderly females | Absolute Count/Absolute Count/Omega api iC/Omega_apip-values | apsy-noARBs elderly females | apsy-ARBs elderly females p-values |
|---|---|---|---|---|---|---|---|---|---|---|---|---|---|---|
| 179 | perception of hallucination, visual | 10019075 | 7,904 | 7,904 | 313 | 3 | 1.575 | -3.573 | 0.02914089 | 149 | 5 | 2.336 | -3.073 | 0.00094354 |
| 394 | dyskinesias a tardive dyskinesia | 10043118 | 22,950 | 22,950 | 1028 | 31 | 1.752 | -0.597 | 0.92596726 | 234 | 23 | 1.449 | -0.697 | 0.999999 |
| 435 | dyskinesias a hypokinesia | 10021021 | 4,795 | 4,795 | 113 | 8 | 0.826 | -0.359 | 0.026039 | 44 | 6 | 1.297 | -1.365 | 0.45113879 |
| 185 | dyskinesias a akathisia | 10001540 | 5,607 | 5,607 | 611 | 3 | 3.035 | -4.513 | 3.09E-05 | 96 | 6 | 2.197 | -2.026 | 0.39220396 |
| 78 | dyskinesias a extrapyramidal disorder | 10015832 | 19,793 | 19,793 | 796 | 14 | 1.597 | -1.657 | 0.04529882 | 305 | 48 | 2.045 | 0.192 | 0.00342332 |
| 938 | dyskinesias a tardive akinesia | 10001541 | 841 | 841 | 49 | 4 | 2.132 | -0.577 | 0.06902725 | 29 | 8 | 3.207 | 0.132 | 0.01484962 |
| 50 | perception of hallucinations, mixed | 10019079 | 1,514 | 1,514 | 129 | 4 | 2.69 | -1.727 | 0.79750395 | 19 | 7 | 1.671 | 0.423 | 0.00314339 |
| 87 | dyskinesias a dyskinesia | 10013916 | 17,270 | 17,270 | 990 | 23 | 2.108 | -1.057 | 0.2587743 | 266 | 38 | 2.044 | -0.055 | 0.03335817 |

FIG. 28

| Adverse Events Class | Adverse Events | Code | Count | Total_Adverse | Relative Risk aspy-ARBs adult females | Relative Risk_aspy-ARBs_adult females | fold reduction using apsy+ARBs | Relative Risk_apsy+ARBs_a | Relative Risk aspy-ARBs elderly females | Relative Risk_apsy+ARBs_elderly females | fold reduction using apsy+ARBs elderly females |
|---|---|---|---|---|---|---|---|---|---|---|---|
| | | | | 63 ms 77,360 | 63 ms 2,329 | | 71 ms 21,729 | 78 ms 2,134 | | | |
| dyskinesias and movement disorde | tardive dyskinesia | 10043118 | 22,950 | 22,950 | 35.702 | 13.54 | | 2.63677991 | 14.873 | | 1.54985544 |
| perception disturbances [45,901] | hallucination, visual | 10019075 | 7,904 | 7,904 | 4.873 | 1.091 | | 4.46654445 | 1.197 | | 2.59231412 |
| dyskinesias and movement disorde | hypokinesia | 10021021 | 4,795 | 4,795 | 1.186 | 3.938 | | 0.30116811 | 2.447 | | 0.45157336 |
| dyskinesias and movement disorde | extrapyramidal disorder | 10015832 | 19,783 | 19,783 | 21.14 | 6.982 | | 3.02778373 | 24.09 | | 1.29705272 |
| perception disturbances [45,901] | hallucination, auditory | 10019070 | 6,855 | 6,855 | 17.275 | 6.889 | | 2.50762084 | 1.833 | | 2.08801746 |
| dyskinesias and movement disorde | akathisia | 10001540 | 5,607 | 5,607 | 10.217 | 1.817 | | 5.62300495 | 8.558 | | 3.19221781 |
| dyskinesias and movement disorde | dyskinesia | 10013916 | 17,270 | 17,270 | 4.382 | 3.396 | | 1.28020271 | 6.671 | | 0.59376405 |
| dyskinesias and movement disorde | movement disorder | 10028035 | 13,523 | 13,523 | 1.073 | 2.511 | | 0.42731979 | 1.436 | | 0.71250159 |
| perception disturbances [45,901] | hallucination | 10019063 | 27,096 | 27,096 | 3.784 | 2.279 | | 1.66037736 | 3.145 | | 0.82290732 |

FIG. 29

SYSTEM AND METHOD FOR DATA MINING VERY LARGE DRUGS AND CLINICAL EFFECTS DATABASES

CROSS-REFERENCE TO RELATED APPLICATIONS

This patent application is a National Stage Application of international patent application PCT/US2016/012208 filed Jan. 5, 2016, which claims priority to U.S. provisional patent application 62/099,923 filed Jan. 5, 2015, the disclosures of which are incorporated by reference in their entirety.

TECHNICAL FIELD

The present disclosure relates to the fields of bioinformatics, pharmacoinformatics, and pharmacovigilance. More particularly, the present disclosure relates to mining one or more clinical databases using iterated, ontological searches among drug-based and phenotype-based ontologies.

BACKGROUND

Pharmacovigilance involves the collection, detection, assessment, monitoring, and prevention of adverse events with pharmaceuticals. The Mayo Clinic reports that up to 70 percent of Americans take prescription drugs, more than half take two prescription drugs, and up to 20 percent of patients take five or more. Polypharmacy plays a central therapeutic role in the treatment of complex, multifactorial disorders but also exposes patients to elevated risks of drug-drug interactions ("DDIs"). Nearly a million injuries or deaths are attributed to adverse events, 30% of which are DDI-related. Novel drug-associated adverse effects may be evident post-approval, leading to patient safety concerns and possibly withdrawal of drugs by the U.S. Food and Drug Administration ("FDA"). For instance, troglitazone with withdrawn in 2000 due to increased risk of hepatotoxicity, while cerivastatin was withdrawn in 2001 due to increased risk of rhabdomyolysis. These effects may be missed during clinical trials, which stress the importance of post-approval pharmacovigilance. Concomitant drugs may also be inadvertently introduced to patient-drug regimen in response to multiple clinical indications, thereby exacerbating the risk of DDI-associated adverse events. This may occur more often when a patient sees multiple clinicians. Pharmacologic adverse events, therefore, provide a strong incentive for reporting clinical indications, drug exposures, and both short and long-term clinical outcomes.

The FDA and the World Health Organization ("WHO") are two exemplary institutions worldwide that pursue pharmacovigilance and monitor safety standards of approved drugs on the market. The FDA maintains the Adverse Events Reporting System ("FAERS"), which stores manually-reviewed adverse event reports received by the FDA from healthcare professionals, manufacturers, and consumers from the United States and around the world. Each patient report contains one or more demographic details such as age and gender, clinical indications, drugs, adverse events, and outcomes. These reports are made available with the principal goal of identifying of latent risks of approved therapeutics and their combinations. The spontaneous nature of FAERS suggests a likelihood of data redundancies and duplications; however, with a combination of prudent data-cleaning mechanisms, duplication removal, and adoption of variety of data-driven approaches, the FAERS data has shown significant phenome-pharmacome associations capable of generating testable hypotheses.

Existing FAERS-mining web-data resources such as the Drugcite service, the AdverseEvents service, the FDAble service, and the OpenVigil service use standard pharmacovigilance approaches to highlight drug-adverse event associations and are limited to basic queries. Several services make use of a proportional reporting ratio, which is a measure of the frequency with which a particular adverse event is reported for a drug of interest versus the frequency with which the same adverse event is reported for drugs in a comparison group (which may comprise a second particular drug, a class of drugs, etc.). The AERS Spider service provides interactive exploration of drug-adverse event relationships by removing disproportionately distributed mask factors, since the use of a proportional reporting ratio without accounting for these mask factors may lead to inaccurate inferences about drug-adverse event relationships. However, these resources do not provide the capability of ontological aggregations and high-dimensional cohort-based analyses to identify potential risk-augmenting drug interactions in population subgroups. In comparison, AERSMine aggregates FAERS data into mineable matrices from mutually exclusive sets and allows for exploratory and investigative analyses to generate testable hypotheses. Further, AERSMine, unlike other available resources, allows one to conduct large-scale, population subgroup-specific studies across multiple treatments and indication cohorts, to recognize inter-correlations, and to make cross-comparisons for better understandings of therapeutic toxicities associated with pharmacological agents. AERSMine-facilitated hypotheses and safety signals can be further reviewed by consortia such as SONAR, and enable additional AE-specific investigations. Reporting back such findings to the FDA can initiate the process of more closer and systematic scrutiny of drug-related novel AEs, ultimately warranting changes in the drug labels. For instance, safety concerns identified and reported to the FDA by SONAR (such as (a) Reye's syndrome for acetylsalicylic acid; (b) pure red cell aplasia for erythropoietin; and (c) nephrogenic systemic fibrosis for gadodiamide) are accurately detected via AERSMine. The complementary nature of AERSMine and SONAR, and the importance of SONAR clinical review, will be valuable for pharmacovigilance.

SUMMARY

The current system and method allow data-driven hypothesis generation to identify potential therapeutic candidates for the treatment of any disease phenotype. The current system and method allow this by identifying drugs and clinical indications that are strongly associated with lower occurrence frequency of disease-associated phenotype by a drug or a drug class. The output of the method and system also provide the ability for comparisons across multiple drug and indication/adverse-event groups. To accomplish these results, the system and method perform an iterated ontological subspace search among drug-based and phenotype-based ontologies for cohorts among the ontologies against which a clinical database of patient information is searched. The results of the search may be mapped both locally (e.g., within a subspace—a therapeutic class or population group, etc.) and globally (across the entire dataset) to identify differentially effective and/or ineffective medication groups; and the results of the search may also be mapped both locally and globally to identify differentially risky and/or less-risky medication groups associated with a clinical indication, treatment or event.

In an embodiment, a system for mining cumulative clinical adverse events data for improved understanding of differential clinical outcomes includes: (1) a pharmacological hierarchical ontology of drug identifications; (2) a phenotype hierarchical ontology of clinical adverse effects and clinical indications; (3) a clinical record database comprising records containing clinical event information; (4) a database mining engine; and (5) an output mapping engine.

The records in the clinical record database may include (a) demographic information for the patient experiencing the clinical event, (b) clinical indication information for the patient experiencing the clinical event, (c) drug identification information associated with the clinical event, (d) adverse event information associated with the clinical event, and (e) patient outcome information (including long-term clinical information).

To map correlations between drugs and adverse events, the database mining engine may be configured to iteratively progress through a selected portion (e.g., a subgroup) of each of the pharmacological hierarchical ontology and the phenotype hierarchical ontology to iteratively select respective pairs of cohort entries from each ontology; and for each pair of cohort entries, query the clinical record database for database records matching the items in the pair of cohort entries. Using these returned results, the mapping engine may be configured to map each pair of cohort entries into a matrix comprising a drug-event cell for each pair of cohort entries and apply a value to each cell, which value is a function of the number of drug-event database records matching a number of items returned by the database mining engine for the corresponding cohort entries. In this manner, simultaneous investigation of cohort-specific differential effects is enabled.

To map drug-drug interactions with adverse events, the database mining engine may be configured to iteratively progress through at least the selected portion (e.g., subgroup) of each of the pharmacological hierarchical ontology and the phenotype hierarchical ontology to iteratively select respective sets of cohort entries, where each set includes a first and second entry from the pharmacological hierarchical ontology and further includes an entry from the phenotype hierarchical ontology (so there is a drug(s)-drug(s)-adverse event(s) triplet). For each set of cohort entries (e.g., triplet+demographics+indications), the database mining engine may query the clinical record database for database records matching the items in the set of cohort entries. Using these returned results, the mapping engine may be configured to map each set of cohort entries into a data matrix comprising a cell for each set of cohort entries, and apply a drug-drug-event interaction value to each cell which is a function of the number of database records matching a number of items returned by the database mining engine for the corresponding cohort entries.

Embodiments of the mapping engine may be configured to display the plurality of cells in at least one of the following visual formats: a heat map, a correlation plot, a bar chart, a circular plot, and a tag cloud. Alternatively, or in addition, embodiments of the mapping engine may be configured to specifically and visually highlight those of the plurality of cells that show under-represented and/or over-represented adverse event information.

With respect to mapping correlations between drugs and adverse events, the mapping engine is configured to apply a normalized, per "x" number of patients value to each cell (e.g., per 1000) corresponding to numbers of drug-event records returned by the database mining engine. Alternatively, the mapping engine may be configured to apply a relative risk value to each cell, wherein the relative risk value pertains to the relative risk of the adverse effects being associated with the corresponding drug identification cohort pair. Alternatively, the mapping engine may be configured to apply a normalized risk value to each cell, wherein the normalized risk value pertains to the relative risk of the adverse effects being associated with the cohort drug.

The relative risk 'RR' value may be calculated for each cell based upon the equation, $$RR = \frac{\left(\frac{a}{a+b}\right)}{\left(\frac{c}{c+d}\right)}$$

where 'a' corresponds to the number of records in the database found by the database mining engine in which the drug identification from the corresponding pair of cohort entries is present and the adverse effects and clinical indications entry from the corresponding pair of cohort entries is also present; where 'b' corresponds to the number of records in the database found by the database mining engine in which the drug identification from the corresponding pair of cohort entries is present and the adverse effects and clinical indications entry from the corresponding pair of cohort entries is not present; where 'c' corresponds to the number of records in the database found by the database mining engine in which the drug identification from the corresponding pair of cohort entries is not present and the adverse effects and clinical indications entry from the corresponding pair of cohort entries is present; and where 'd' corresponds to the number of records in the database found by the database mining engine in which the drug identification from the corresponding pair of cohort entries is not present and the adverse effects and clinical indications entry from the corresponding pair of cohort entries is also not present.

In such a system, the mapping engine may be configured to provide the following visual indications to the cell based upon the calculated relative risk value 'RR': a first visual indication corresponding to a minimal risk if RR is calculated to be less than or equal to 1 (e.g., a blue color shade); a second visual indication corresponding to a moderate risk if RR is calculated to be greater than 1 and less than or equal to 2 (e.g., a white or clear color shade); and a third visual indication corresponding to a high risk if RR is calculated to be greater than 2 (e.g., a darker shade of red). The visual indications may appear as if on a spectrum; for example, where the visual indications are colors, the colors may darken or lighten to indicate the values more precisely (as compared to showing three colors/indications with no in-between variation).

The normalized risk value 'IC' may be calculated for each cell based upon the equation, $$IC = \log_2((AE\_Count \ast T)/(Unique\_Patients \ast AE\_Total))$$

where 'T' corresponds to the total number of records in the database; where 'AE_Count' corresponds the number of records in the database found by the database mining engine in which the drug identification from the corresponding pair of cohort entries is present and the adverse effects and clinical indications entry from the corresponding pair of cohort entries is also present; where 'AE_Total' corresponds the number of records in the database found by the database mining engine in which the adverse effects and clinical indications entry from the corresponding pair of cohort entries is present; and where Unique_Patients corresponds the number of records in the database found by the database mining engine in which the drug identification from the corresponding pair of cohort entries is present (in an embodiment, Unique_Patients may factor non-duplication of patients—that is, by correcting for duplication, even if a patient report includes more than one adverse event for a drug, the embodiment may consider the patient once for the analysis).

In such a system the mapping engine may be configured to provide the following visual indications to the cell based upon the calculated normalized risk value 'IC': a first visual indication corresponding to drug-events database records being less than expected if IC is calculated to be less than 0 (e.g., a blue shade); a second visual indication corresponding to drug-events database records being more than expected if IC is calculated to be greater than 0 (e.g., a red shade); and a third visual indication corresponding to drug-events being as expected if IC is calculated to be equal to 0 (e.g., a clear or white shade).

The drug-drug-event interaction value 'Ω' for each cell may be calculated from the following equation, $$\Omega = \log_2((n_{111} + \text{alpha})/(E_{111} + \text{alpha}));$$

where '$n_{111}$' corresponds to the actual occurrences of the drug-drug-event interaction returned by the mapping engine; where '$E_{111}$' corresponds to expected occurrences of the drug-drug-event interaction; and where 'alpha' corresponds to a tuning parameter. The "$_{111}$" represents the presence of drug/drug class A, drug/drug class B, and adverse event. Hence, $n_{111}$ represents the observed drug-drug-adverse event triplet, and $E_{111}$ represents the expected drug-drug-adverse event triplet. In such a system the mapping engine may be configured to provide the following visual indications to the cell based upon the calculated drug-drug-event interaction value 'Ω': a first visual indication corresponding to drug-drug-events being less than expected if Ω is calculated to be less than 0 (e.g., a blue color shade); a second visual indication corresponding to drug-drug-events being more than expected if Ω is calculated to be greater than 0 (e.g., a red color shade); and a third visual indication corresponding to drug-drug-events being as expected if Ω is calculated to be equal to 0 (e.g. a white or clear color shade). A positive Ω may indicate that the two drugs, when used together, increase the risk of the adverse event more than the sum of the risks attributable to each drug separately. A negative Ω may indicate that the two drugs, when used together, decrease the risk of the adverse event less than the sum of the risks attributable to each drug separately.

With respect to the database mining engine utilizing subgroups to narrow the mining window within the clinical record database, such subgroups can pertain to demographic criteria, clinical information criteria, drug identification criteria, adverse event criteria, and/or patient outcome criteria (including long-term indication criteria). Such subgroups may also pertain to a combination of such criteria and/or multiples of such criteria. In an embodiment, the mapping engine may be configured to display a comparison of values in the cells associated with the subgroup (local representation) versus cells associated with a global representation of the database records. In another embodiment, the mapping engine may be configured to display a comparison of values in the cells associated with a first subgroup versus cells associated with a subgroup of the database records.

With respect to the pharmacological hierarchical ontology of drug identifications, such ontology may be ordered under a multitude of parent concepts, a multitude of generic pharmacological concepts under the parent concepts, and, optionally, a multitude of individual drug entries under the generic pharmacological concepts. The generic pharmacological concepts may present the most granular data—any entries under the generic pharmacological concept could be variations in the salts of a drug, such as citrate, sodium, etc. The drug identifications in this ontology may include a plurality of drug entries, where each drug entry may include several or many names for each drug such as: clinical names for the drug, commercial brand names for the drug, molecular names for the drug, foreign names for the drug, spelling variants for the drug, and/or misspellings for the drug. For example, the Anatomical Therapeutic Chemical ("ATC") classification system employed by the World Health Organization may be used to structure a pharmacological hierarchical ontology of drug identifications.

With respect to the phenotype hierarchical ontology, this ontology may be ordered, for example, under a multitude of hierarchical MedDRA concepts. MedDRA refers to The Medical Dictionary for Regulatory Activities developed by the International Council for Harmonization of Technical Requirements for Registration of Pharmaceuticals for Human Use. MedDRA includes a highly specific, standardized, hierarchical, maintained medical terminology and covers medical products such as pharmaceuticals, biologics, vaccines, and drug-device combination products.

A current embodiment of the current disclosure, identified as AERSMine, is a platform to mine the FAERS data and facilitate high-resolution analyses through (a) implementation of signal detection algorithms that serve to identify significant drug-adverse event (IC) or drug-drug-adverse event (Ω) associations; (b) integration of adverse event and drug ontologies; and (c) creation of sets, a unique feature that allows complex querying of adverse events (e.g., selective exclusion of drugs and co-existing or confounding indications for simultaneous investigation of adverse interactions). The adverse event ontology may be based on the MedDRA, and the drug ontology may be based on the ATC classification. The analyzable matrices can be displayed as absolute counts, normalized reports per 1000 patients, relative risks, drug-adverse event, and drug-drug-adverse event signals, and they can be exported in tab-separated files or readily visualized within AERSMine as may be facilitated by canvasXpress, a standalone HTML5 library that includes simple and unobtrusive graphing capability, or other visualization components/graphing libraries.

BRIEF DESCRIPTION OF THE DRAWINGS

The foregoing and other features of the present disclosure will become more fully apparent from the following description and appended claims, taken in conjunction with the accompanying drawings. Understanding that these drawings depict only certain embodiments in accordance with the disclosure and are, therefore, not to be considered limiting of its scope, the disclosure will be described with additional specificity and detail through use of the accompanying drawings.

In the drawings:

FIG. 3 illustrates exemplary patient records that may be found in a clinical record database;

FIG. 11 provides an example user interface through which a user may select indications/adverse events or indication/adverse event classes from the phenotype hierarchical ontology;

FIG. 12 provides an example user interface through which a user may limit the analysis to a specific demographic of patients;

FIG. 13 provides an example user interface through which a user may instruct the mapping engine to provide various filters to an analysis and/or results;

FIG. 14A illustrates a portion an exemplary high-resolution matrix that captures sub-cohort based differential responses to a wide-array of cardiovascular system drugs;

FIG. 14B illustrates another portion an exemplary high-resolution matrix that captures sub-cohort based differential responses to a wide-array of cardiovascular system drugs;

FIG. 20 provides another example output from a mapping engine in the form of a drug recommendation table for a particular combination of mapped factors;

FIG. 21 illustrates inputs useful for calculating relative risk;

FIG. 22 the illustrates inputs useful for calculating the normalized risk value Information Component;

FIG. 23A is a portion of a map displaying relative risks;

FIG. 23B is another portion of a map displaying relative risks;

Figure 26:
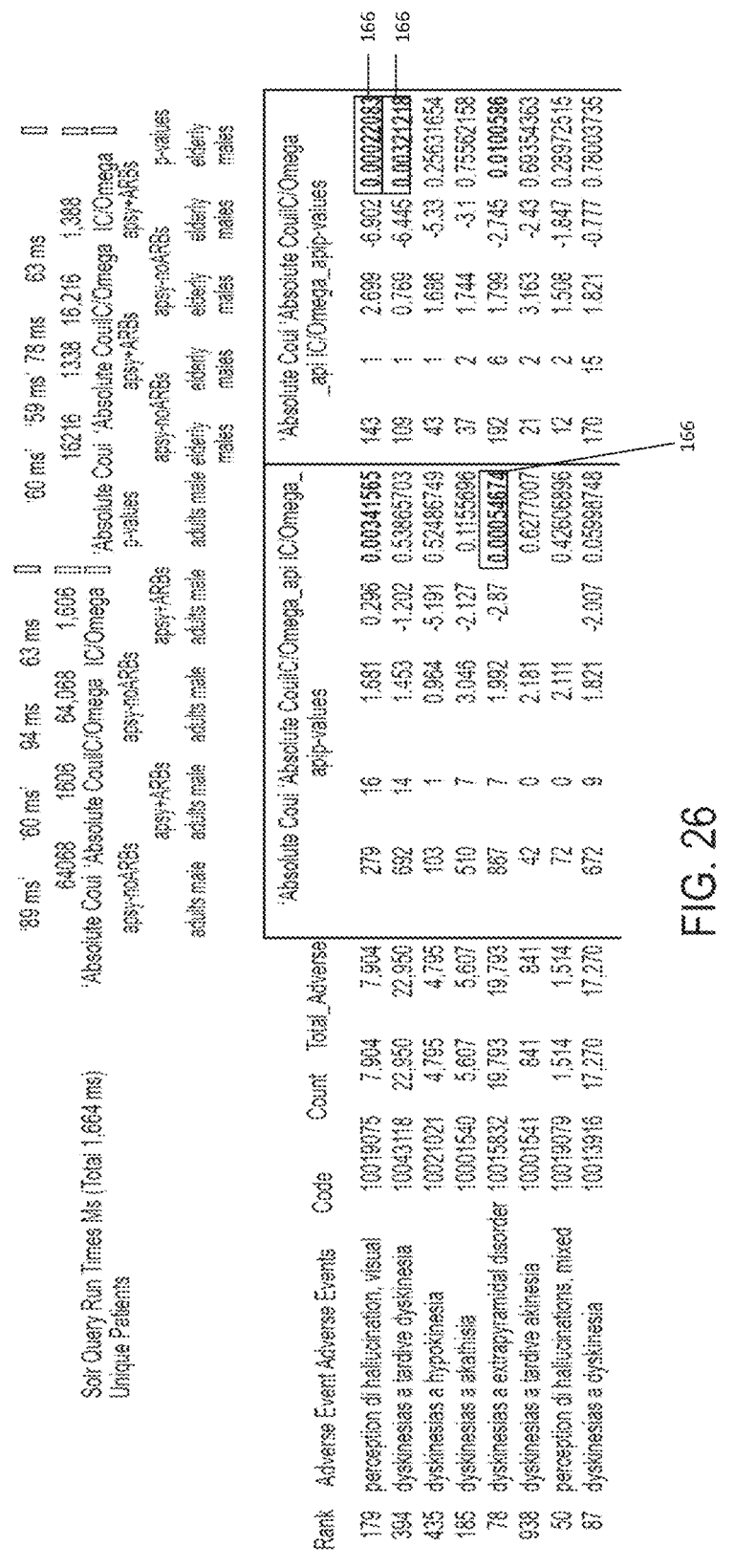

FIG. 26 provides a portion of a results output tending to show promising results when angiotensin receptor blockers are added to the therapeutic regimen of patients on antipsychotics;

FIG. 28 provides another portion of a results output tending to show promising results when angiotensin receptor blockers are added to the therapeutic regimen of patients on antipsychotics;

FIG. 29 provides another portion of a results output tending to show promising results when angiotensin receptor blockers are added to the therapeutic regimen of patients on antipsychotics;

DETAILED DESCRIPTION OF EXEMPLARY EMBODIMENTS

Figure 1:
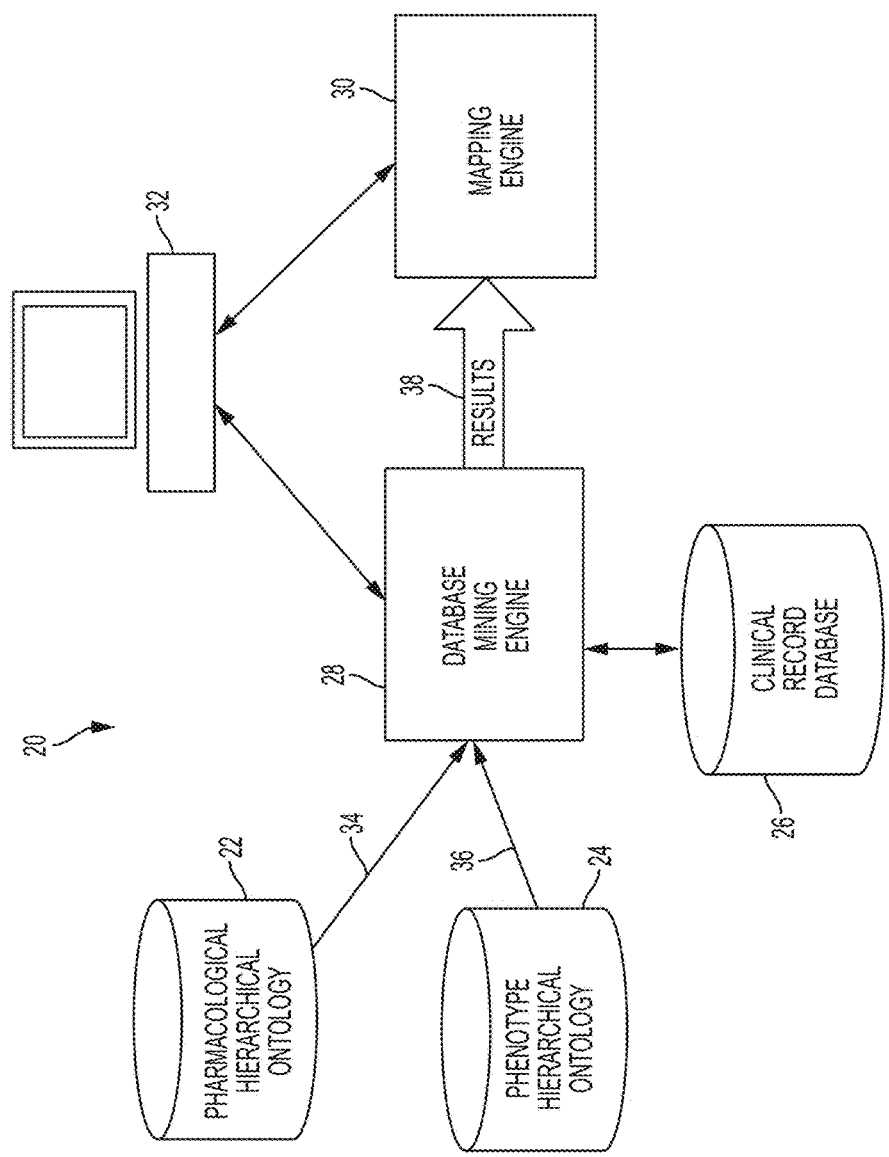
FIG. 1 is a schematic diagram illustrating the system of the present disclosure.

Adverse drug effects, reactions, or events ("adverse events") provide a strong incentive for centralized reporting of drug histories, adverse responses, and the clinical background for having used medications in the first place. Leveraging the cumulative records of the FDA's Adverse Events Reporting System, or FAERS, embodiments of the current disclosure utilize a data-normalization and data-mine-creation strategy that could enable the carrying out of comparative analyses of multiple cohorts as a function of indications and/or therapeutics for differential reporting of clinical outcomes as based on all reported adverse events. The exemplary embodiment, coined AERSMine, is a multi-cohort, data-mining platform that may be used to analyze millions of adverse event reports and to recognize the risk of life-threatening, drug-induced complications while also allowing for the identification of key, under-represented groups that signify inverse, drug-adverse event correlations characteristic of latent beneficial effect. AERSMine generates viewable and/or analyzable data matrices that can be filtered and scored using well-established safety signal detection metrics, clustered, and visualized to recognize data patterns. The ultimate goals of these analyses are to safeguard patients by improving therapeutic selections and monitoring strategies in addition to protecting valuable therapeutics by minimizing harmful interaction choices. A version of AERSMine allows high-resolution data mining across a database of over 4.3 million adverse event reports—

126,579 children (aged 0-14), 154,256 young adults (aged 15-24), 1,547,638 adults (aged 25-65), 842,486 elderly (aged 66+), and 1,614,136 unspecified (age/gender not specified to the database). A particular version of AERSMine allows high-resolution data mining across the FAERS database, which contains millions of records and is ever-increasing.

Transforming the FAERS data into a well-organized, mineable form has been a persistent challenge in the art, but AERSMine provides a transparent framework that allows simultaneous querying of therapeutics, indications, and adverse events across population subgroups and facilitates high-resolution analyses. In addition, by incorporating the World Health Organization quantitative safety signal algorithms, AERSMine allows exploratory analysis, safety signal detection, and discovery of new therapeutics and drug repositioning candidates through simultaneous investigation of multiple patient subgroups. This high-dimensional analysis has the potential to generate testable hypotheses, which may recognize potential candidate factors that alter the risk of adverse complications. It is essentially the latent content of these data that has the potential to reveal unexpected clinical outcomes associated with different drug regimens, and that by numbers and its open aperture approach, vastly exceeds the drug-effect information that is obtainable from conventional series of clinical trials or model systems.

Referring to FIG. 1, in an embodiment, a system 20 for mining cumulative clinical adverse events data for improved understanding of differential clinical outcomes includes: a pharmacological hierarchical ontology of drug identifications 22; a phenotype hierarchical ontology of clinical adverse effects and clinical indications 24; a clinical record database comprising records containing clinical event information 26; a database mining engine 28 and an output mapping engine 30. One or more computer user interfaces 32 are operatively connected (electrically coupled, coupled via a direct or indirect data link, or capable of being coupled via a direct or indirect data link) to the database mining engine 28 and the mapping engine 30 for the purpose(s) of setting up an analysis of the clinical record database 26 and for receiving, viewing, and processing specialized outputs and maps (as will be discussed herein) from the mapping engine 30.

Figure 2:
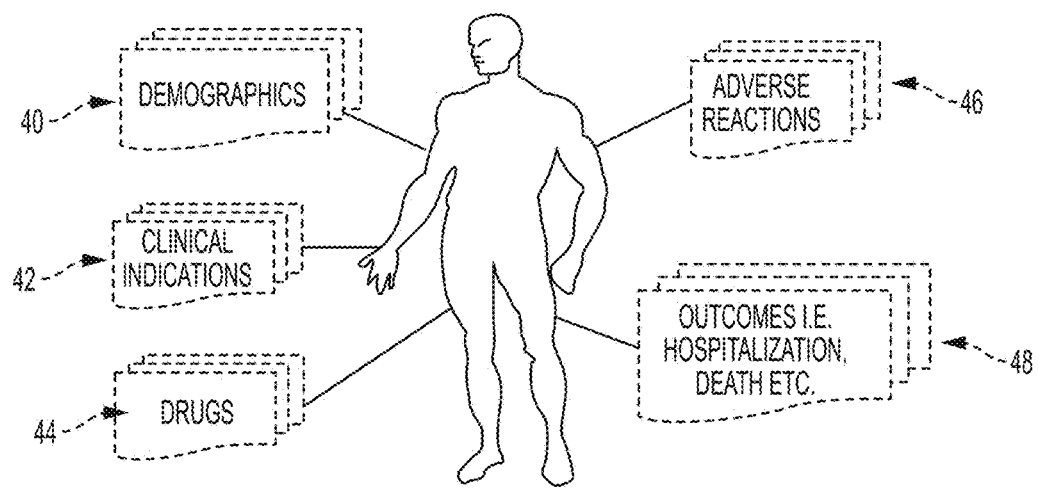
FIG. 2 is a diagram showing the types of information that may be stored and accessed by the system of the present disclosure.
Figure 35:
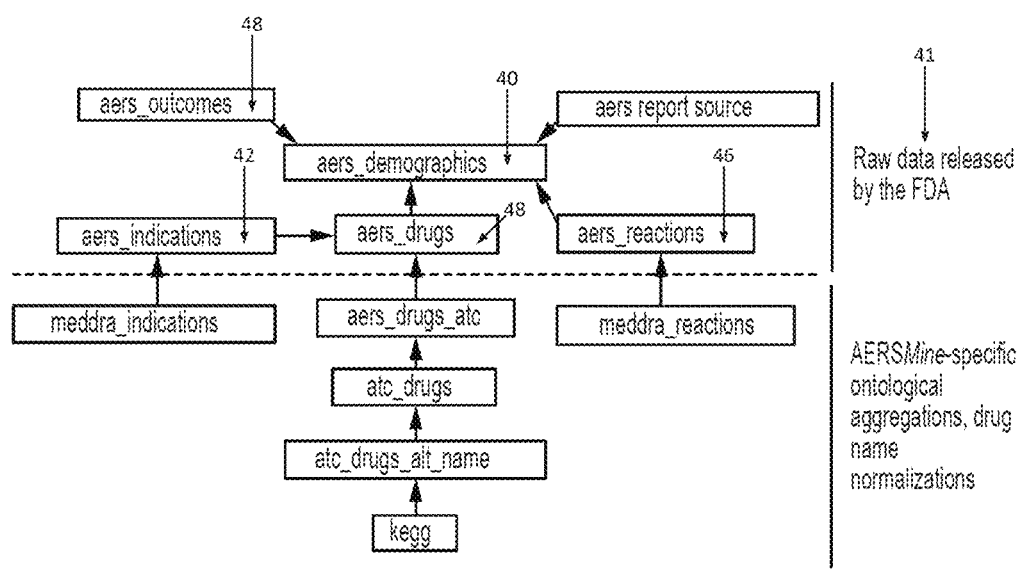
FIG. 35 is a schematic diagram illustrating example ontological aggregations of data that may be found in a clinical record database.

As shown in FIGS. 2, 3, and 35, the records in the clinical record database 26 may include demographic information for the patient experiencing the clinical event 40, clinical indication information for the patient experiencing the clinical event 42, drug identification information associated with the clinical event 44, adverse event information associated with the clinical event 46, and/or patient outcome information 48.

Referring back to FIG. 1, to map correlations between drugs and adverse events, the database mining engine 28 may be configured to iteratively progress through a selected portion (e.g., subgroup) of each of the pharmacological hierarchical ontology 22 and the phenotype hierarchical ontology 24 to iteratively select respective pairs of cohort entries 34, 36 from each ontology; and for each pair of cohort entries 34, 36, query the clinical record database 26 for the database records 38 matching the items in the pair of cohort entries 34, 36. Using these returned results 38, the mapping engine 30 may be configured to map each pair of cohort entries into a matrix comprising a drug-event cell for each pair of cohort entries and apply a value to each cell which is a function of the number of drug-event database records matching a number of items returned by the database mining engine for the corresponding cohort entries.

It is also within the scope of the current disclosure that the database mining engine iteratively progresses through entirety of each or one of the pharmacological hierarchical ontology 22 and the phenotype hierarchical ontology 24 to iteratively select respective pairs of cohort entries from each ontology 34, 36. In other words, it is not necessary that a subgroup be designated for the ontologies to fall within the scope of the current disclosure.

As will be discussed below, with respect to mapping correlations between drugs and adverse events, the mapping engine 30 may be configured to apply a normalized per "x" number of patients value to each cell (e.g., per 1000) corresponding to the number of drug-event records returned by the database mining engine. Alternatively, the mapping engine may be configured to apply a relative risk value to each cell, wherein the relative risk value pertains to the relative risk of the adverse effects being associated with the corresponding drug identification cohort pair. Alternatively, the mapping engine may be configured to apply a normalized risk value to each cell, wherein the normalized risk value pertains to the relative risk of the adverse effects being associated with the cohort drug. Some example output matrices are described below as shown in FIGS. 11-13.

Similarly, to map drug-drug interactions with adverse events, the database mining engine 28 may be configured to iteratively progress through at least the selected portion (e.g., subgroup) of each of the pharmacological hierarchical ontology 22 and the phenotype hierarchical ontology 24 to iteratively select respective sets of cohort entries, where each set includes a first and second entry 34 from the pharmacological hierarchical ontology, and each set includes an entry 36 from the phenotype hierarchical ontology, and, for each set of cohort entries 34, 36, query the clinical record database 26 for the database records matching the items in the set of cohort entries. Using these returned results 38, the mapping engine 30 may be configured to map each set of cohort entries into a matrix comprising a cell for each set of cohort entries, and apply a drug-drug-event interaction value $\Omega$ to each cell which is a function of the number of database records matching a number of items returned by the database mining engine for the corresponding cohort entries 34, 36.

It is also within the scope of the current disclosure that the database mining engine iteratively progresses through the entirety of each or one of the pharmacological hierarchical ontology 22 and the phenotype hierarchical ontology 24 to iteratively select respective sets of cohort entries from each ontology 34, 36. In other words, it is not necessary that a subgroup be designated for the ontologies to fall within the scope of the current disclosure.

With respect to the pharmacological hierarchical ontology of drug identifications, such ontology may be ordered under a multitude of parent concepts and a multitude of generic pharmacological concepts under the parent concepts. The drug identifications in this ontology may include a plurality of drug entries, where each drug entry may include several or many names for each drug such as: clinical names for the drug, commercial brand names for the drug, molecular names for the drug, foreign names for the drug, spelling variants for the drug, and/or misspellings for the drug.

The FDA stores manually reviewed MedDRA-coded indications and adverse events, but the reports allow drug names either as generic names, brand names, or arbitrary entries. MedDRA refers to the Medical Dictionary for Regulatory Activities developed by the International Council for Harmonisation of Technical Requirements for Registration of Pharmaceuticals for Human Use. In addition, unlike the precise and consistently defined indications and adverse events, the drug names are not entirely validated, thereby allowing spelling errors and invalid text to be recorded as 'drug entries'. The spontaneous nature of adverse event reporting may require pre-processing of the patient-reports and adoption of stringent data cleaning, including arbitrary/brand-to-generic drug name unification, in order to allow qualitative analyses of this substantial clinical drug-effects resource.

Figure 4:
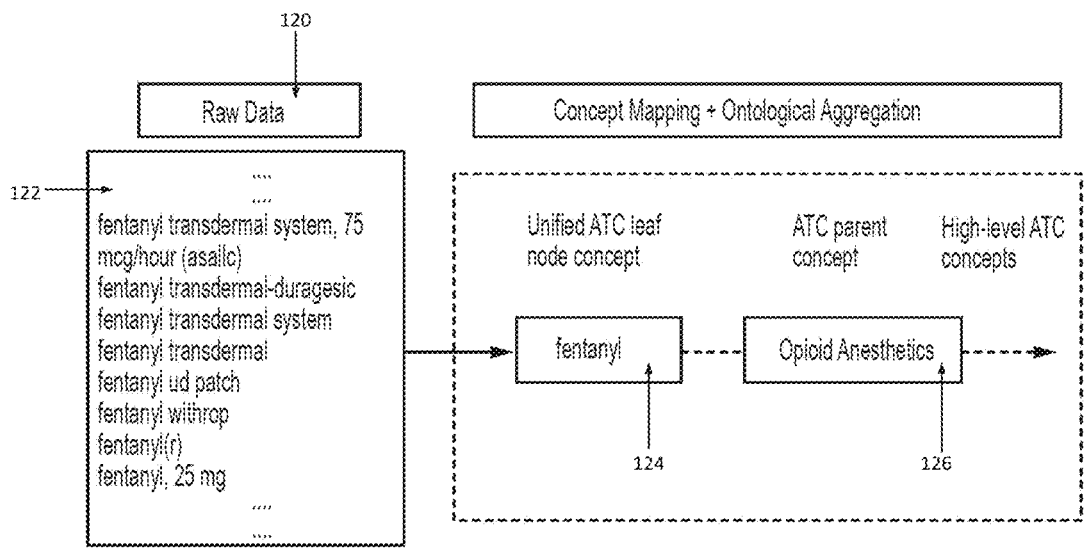
FIG. 4 shows a drug unification and normalization process used to create a pharmacological hierarchical ontology.
Figure 5:
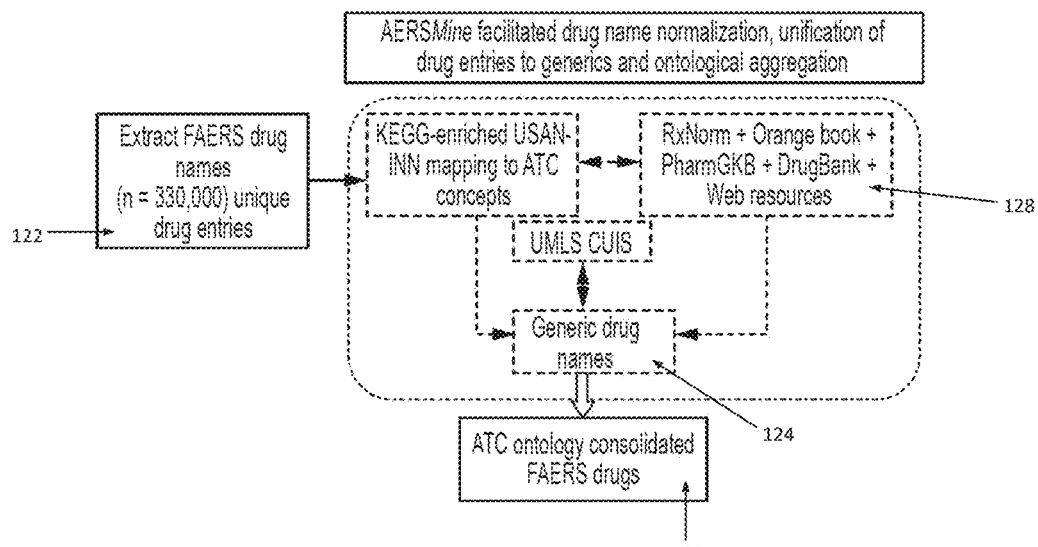
FIG. 5 shows a drug unification and normalization process used to create a pharmacological hierarchical ontology.
Figure 6:
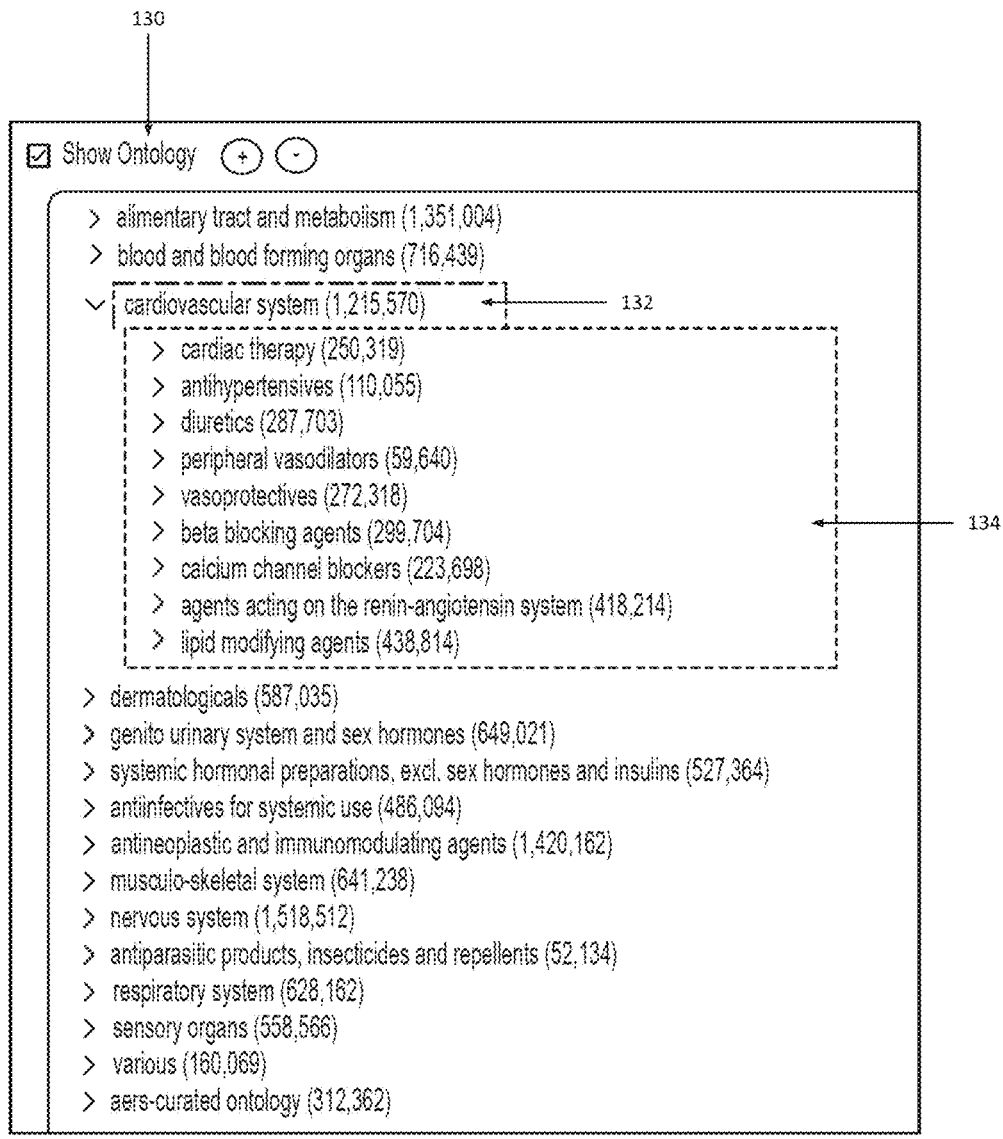
FIG. 6 provides an example view of a portion of a pharmacological hierarchical ontology showing parent concept listings and a plurality of generic pharmacological concepts.

In an exemplary embodiment, a drug normalization and unification process as shown in FIGS. 4 and 5 is performed to consolidate over 20 million drug entries 120 (including ~400,000 unique drug name text entries including brand names, foreign names, spelling variants, and misspellings) to ~4,500 generic pharmacological concepts 124 that were aggregated using ~1,200 parent concepts 126 within the ATC (Anatomical Therapeutic Chemical) ontology 129. Drug name entries that could not be unified to generic names (such as drugs that are awaiting ATC coding and recently approved combinatorial drugs) accounted for approximately 3% of the entries and were aggregated using a custom-curated ontology. To perform this normalization process, the current embodiment utilizes a set of tools encompassing natural language processing (NLP), machine learning, and supervised mapping to unify the drug name entries from the raw data (e.g., from the FAERS data) to their generic names. Other similar tools and techniques may be apparent to those skilled in the art. These tools may rely on existing knowledge bases 128 that include RxNorm, PharmGKB, Drug-Bank, Orange Book, and internal brand-generic mapping. The International Nonproprietary Names and United States Adopted Names variants (including salts) are also unified. Spelling variants and/or typos are also unified using semantic normalization. Drug names that cannot be unified are aggregated using a custom curated ontology. Ontological aggregation improves confidence in association analysis and statistical power. FIG. 6 provides an example view of the pharmacological hierarchical ontology 130 showing parent concept listings 132, such as "cardiovascular system" and "dermatologicals," and a plurality of generic pharmacological concepts 134, such as "diuretics" and "beta blocking agents," under the "cardiovascular system" parent concept. It is within the scope of the present disclosure that one or more of the plurality of generic pharmacological concepts may contain still more specific sub-concepts down to drug-level specificity.

Figure 7:
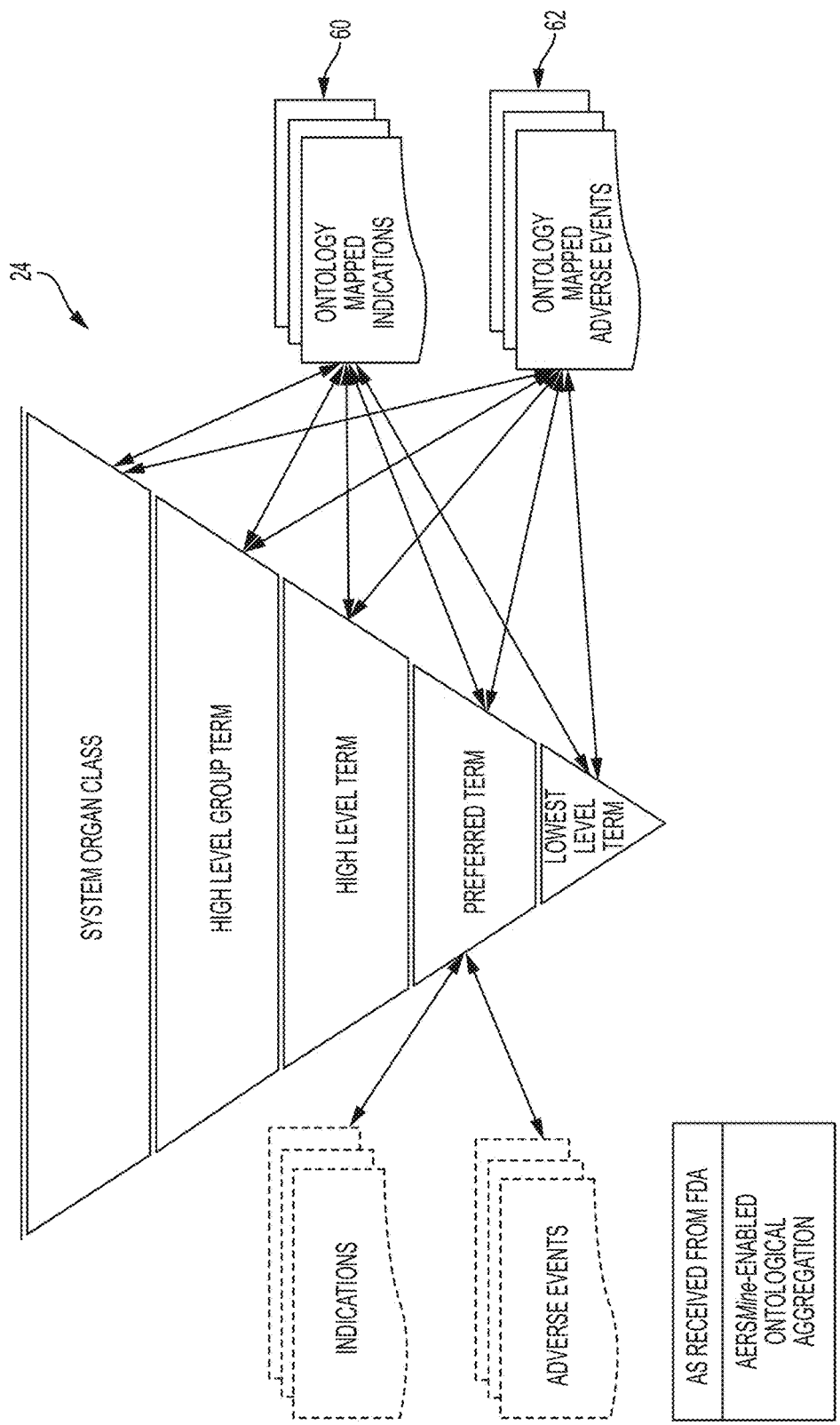
FIG. 7 shows an example organization of a phenotype hierarchical ontology.

With respect to the phenotype hierarchical ontology 24, this ontology may be ordered, for example, under a multitude of hierarchical MedDRA concepts. As shown in FIG. 7, the ontology 24 may include a number of hierarchical levels ordered down from "System Organ Class," to "High Level Group Term," to "High Level Term," to "Preferred Term" down to "Lowest Level Term." As also shown in FIG. 7, this ontology 24 may include a separate Indications Ontology 60 and a separate Adverse Events Ontology 62. In the exemplary embodiment, the unique clinical indications (~10,200) and adverse events (~16,400) were aggregated using approximately 2,000 hierarchical MedDRA concepts that allow complete classification and disease-based aggregation. The FDA codes the clinical indications and adverse events using the MedDRA Preferred Terms (PTs), which are lower level granular concepts. To increase the resolving power of the analyses, indications and reactions were concept-aggregated using the MedDRA 16.1 ontology. This results in higher-level MedDRA concepts to be included such as High Level Terms, High Level Group Terms, and System Organ Classes in addition to PTs. AERSMine thus offers an ontology-based hierarchical grouping of indications and adverse events that significantly allows a researcher to focus on a group of disorders, indications, or reactions.

Figure 8:
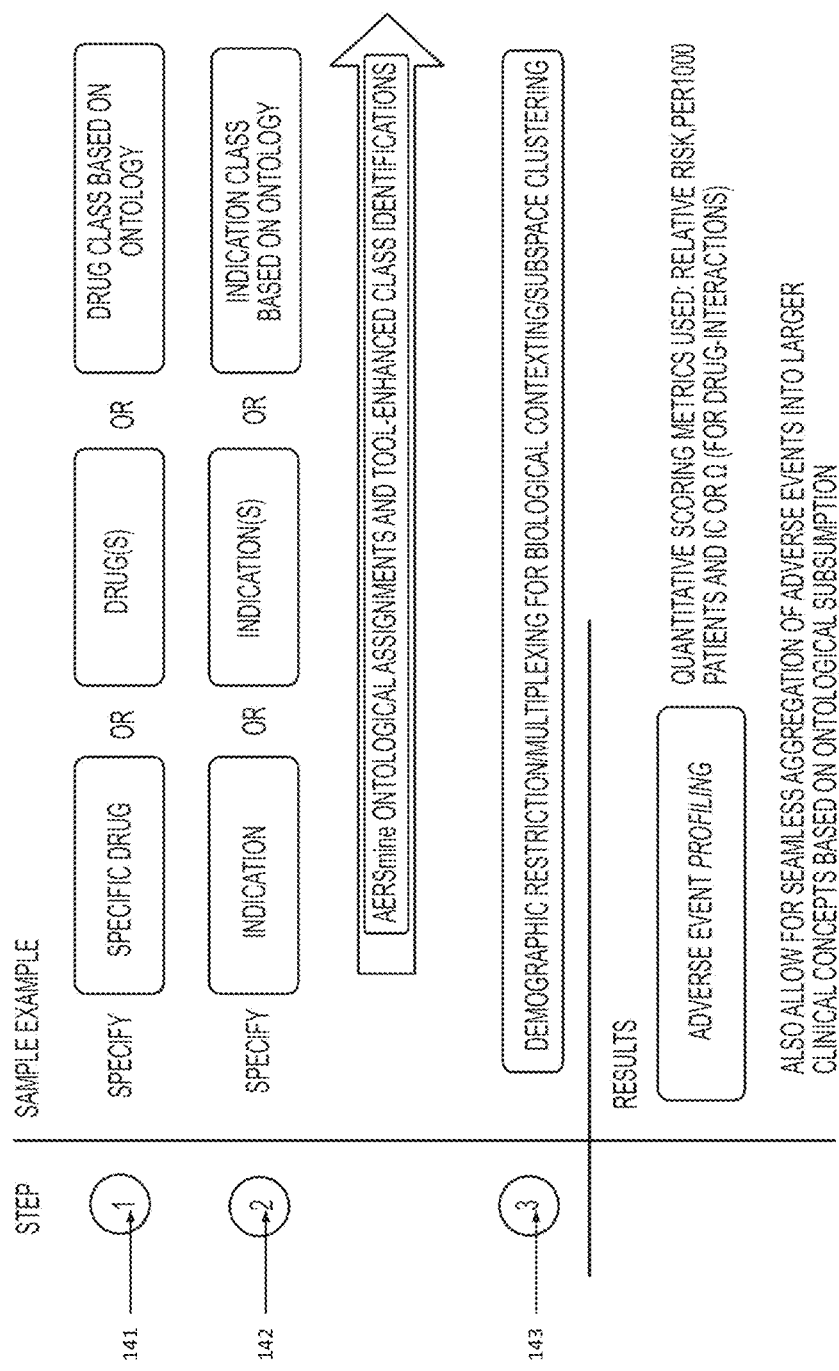
FIG. 8 is a flowchart showing an exemplary process for initiating an analysis using the system of the present disclosure.

Referring to FIG. 8 and FIG. 1, to initiate an analysis according to an exemplary embodiment, the user may start in "Step 1" 141 by specifying, through the user interface 32, a specific drug, a number of drugs or a drug class from the pharmacological ontology 22. Next, in "Step 2" 142, the user will then specify an indication/adverse-event, a number of indications/adverse-events, or an indication/adverse-event class. In "Step 3" 143, a user may specify a subgroup of the clinical record database 26 upon which to perform the analysis. With respect to the database-mining engine, subgroups may be utilized to narrow the mining window within the clinical record database. Such subgroups can pertain to demographic criteria, clinical information criteria, drug identification criteria, adverse event criteria and/or patient outcome criteria. Such subgroups may also pertain to a combination of such criteria and/or multiples of such criteria. In an embodiment, the mapping engine may be configured to display a comparison of values in the cells associated with the subgroup (local representation) versus cells associated with all or substantially all of the of the database records (global representation).

Figure 9:
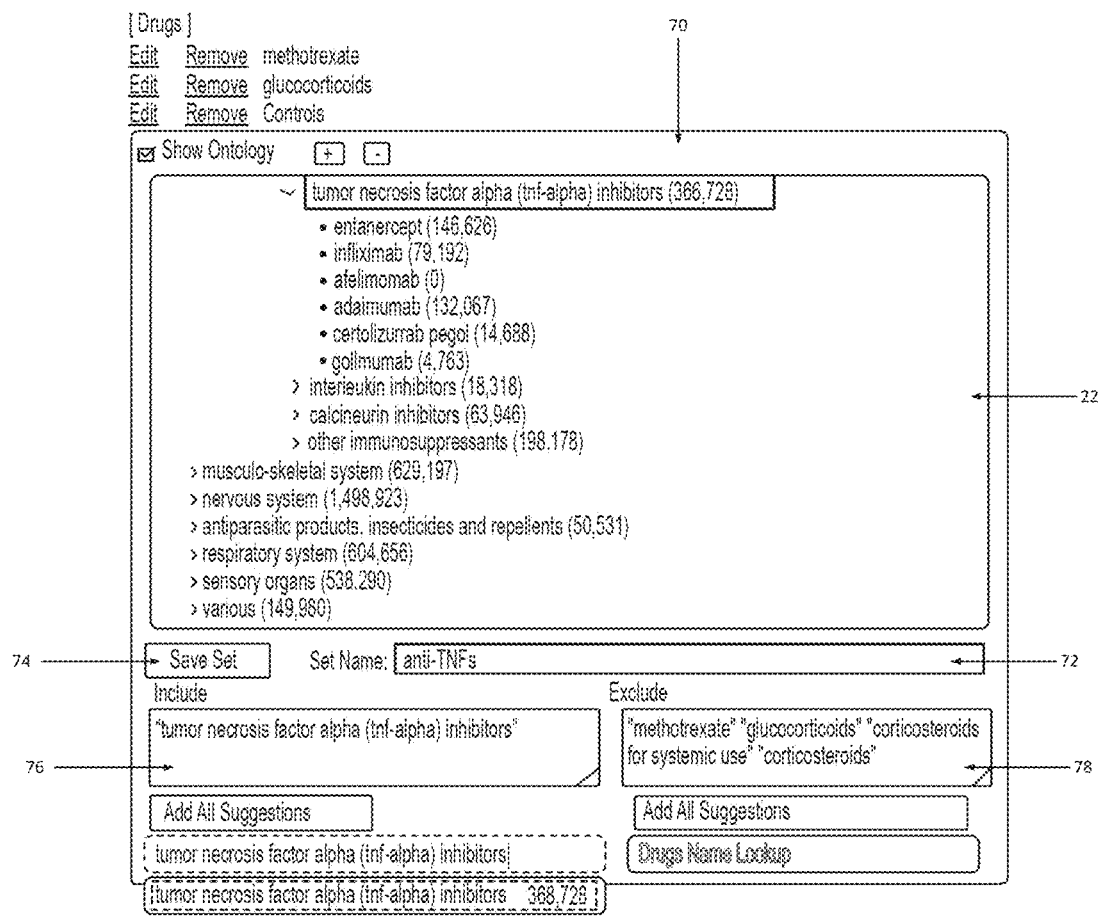
FIG. 9 shows an example user interface through which a user may select specific drug(s) and/or drug classes.
Figure 10:
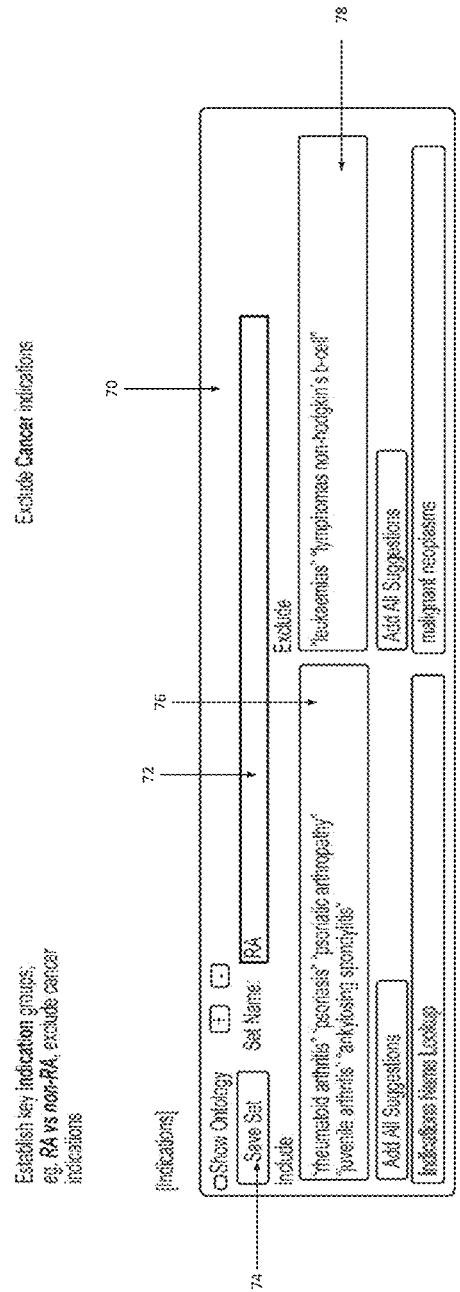
FIG. 10 an example user interface through which a user may select specific drug(s) and/or drug classes.

FIGS. 9 and 10 provide an example user interface through which a user may select specific drug(s) and/or drug classes. The interface may include a window 70 from which a user is able to view and select from portions of the pharmacological hierarchical ontology 22; a field 72 in which the user may be able to name the set of selected drug(s) and/or drug classes along with a button 74 allowing that set to be saved; and a pair of fields 76, 78 in which the user can instruct the database mining engine 28 to respectively include or exclude selections of drug(s) and/or drug classes from the analysis.

FIG. 11 provides an example user interface through which a user may select indications/adverse events or indication/adverse event classes from the phenotype hierarchical ontology 24. This user interface includes a window (not shown) from which a user is able to view and select from portions of the phenotype hierarchical ontology 24; a field 82 in which the user may be able to name the set of selected indication(s)/adverse-event(s) or classes along with a button 84 allowing that set to be saved; and a pair of fields 86, 88 in which the user can instruct the database mining engine 28 to respectively include or exclude selections of indications (s)/adverse-event(s) and/or their classes from the analysis.

FIG. 12 provides an example user interface through which a user may limit the analysis to a specific demographic of patients. A number of check-boxes 89 are provided in which a user may select or deselect various demographic filters.

FIG. 13 provides an example user interface through which a user may instruct the mapping engine 30 to provide various filters 140 such as a column filter 142, an absolute count filter 144, a per 1000 patients filter 146, a relative risk filter 148, a relative risk pValue filter 149, and an IC filter 141. An "Enable" set of check boxes 143 allows the user to enable or disable each filter and a "Filter" column allows the user to set the bounds of each filter.

Embodiments of the mapping engine may be configured to display the plurality of cells in a heat map, a correlation plot, and/or a tag (word) cloud. Alternatively, or in addition, embodiments of the mapping engine may be configured to specifically visually highlight those of the plurality of cells that show under-represented adverse event information.

Figure 15:
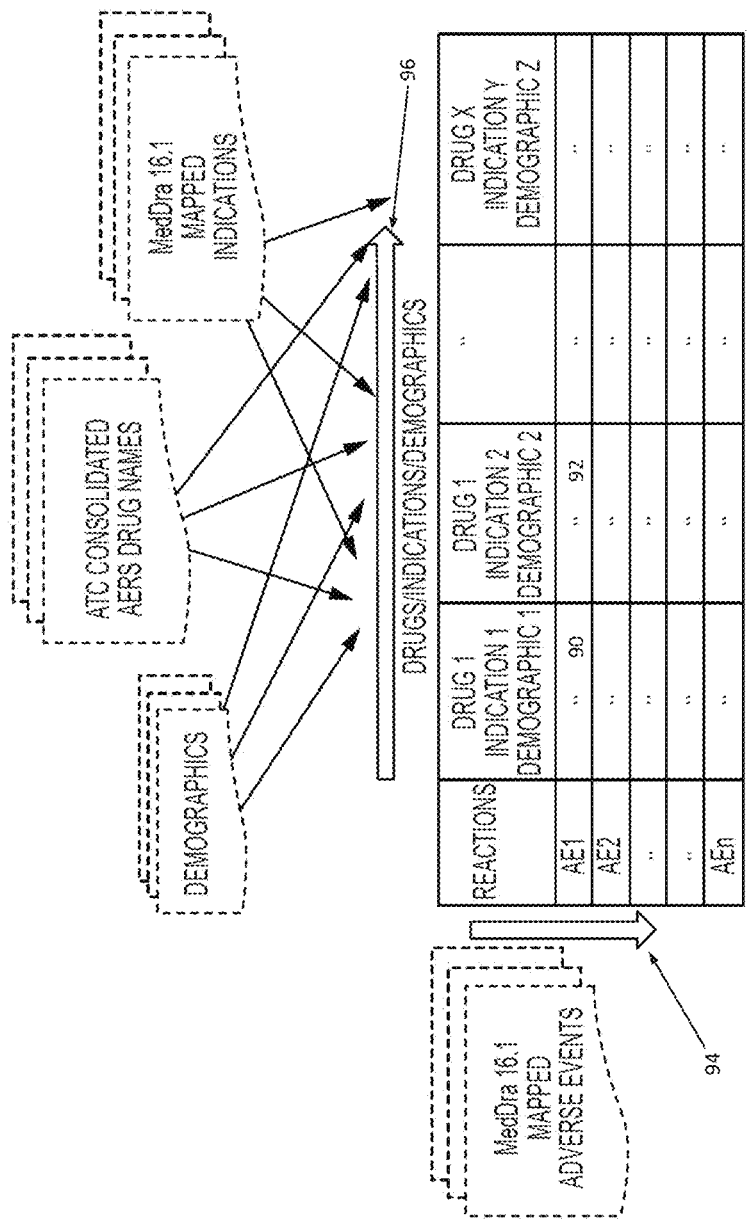
FIG. 15 shows an example map format for displaying results obtained by the system of the present disclosure.

An example map format is shown by FIG. 15. In the example of FIG. 15, each cell provides a calculated value for a specific adverse event (ordered along the vertical axis 94) versus a specific combination of drugs/indications/demographics (ordered along the horizontal axis 96). For example, cell 90 provides a visual indication of a calculated value of adverse event "AE1" occurring with Drug1, Indication1 and Demographic1; while cell 92 provides a visual indication of a calculated value of adverse event "AE1" occurring with Drug1, Indication2 and Demographic2, and so on.

As shown in FIGS. 14A and 14B, a high-resolution matrix captures the sub-cohort based differential response to a wide-array of cardiovascular system drugs including angiotensin receptor blocking agents, beta blocking agents, calcium channel blockers, antithrombotic agents, vasodilators and lipid modifying agents. In this example, a unique adverse event-reporting pattern is seen across a therapeutic class-based cohort—the rows represent the adverse events and columns represent the number of patients reporting the adverse events when they were on either of the therapeutic sub-classes. The ability to create multiple cohorts across any dimension (drugs, clinical indications, adverse events) and study their differential profiles using quantitative safety metrics allows the system of the present disclosure to generate testable hypotheses that address differential outcomes among relatively similar patients following alternative regimens.

Figure 16:
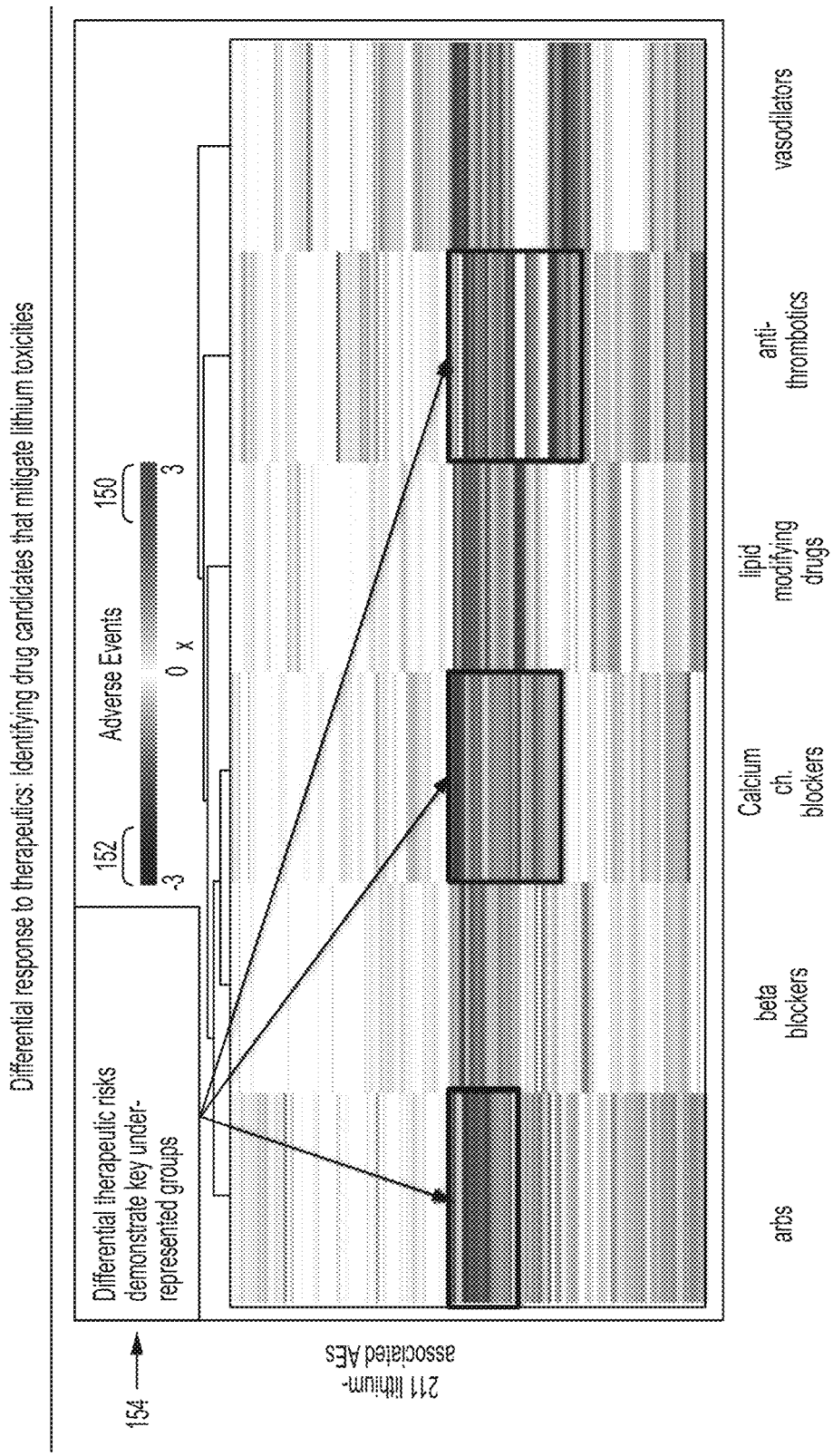
FIG. 16 is an exemplary heat map with highlighted portions indicating a relatively lower risk of an adverse event occurring.
Figure 17:
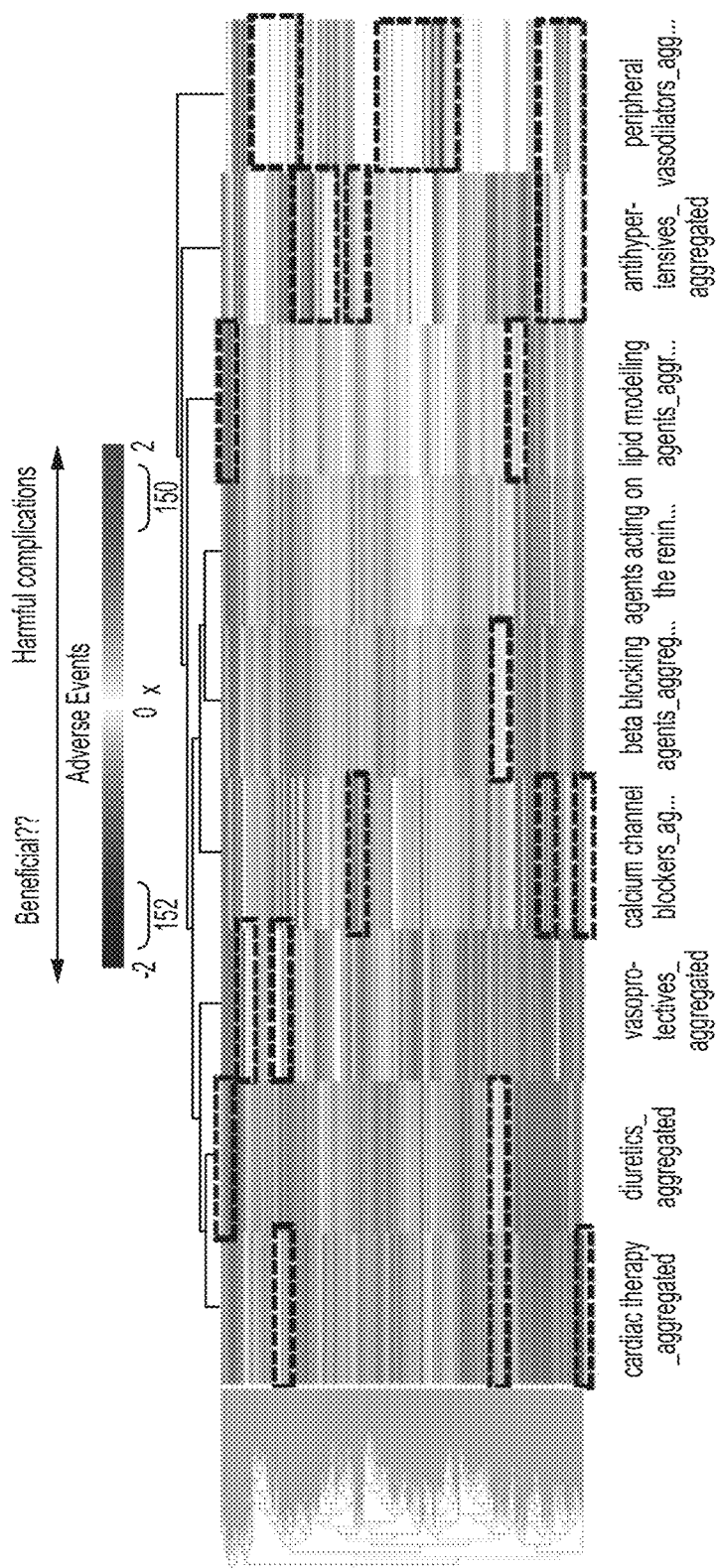
FIG. 17 is an exemplary heat map with highlighted portions indicating a relatively lower risk of an adverse event occurring.
Figure 25:
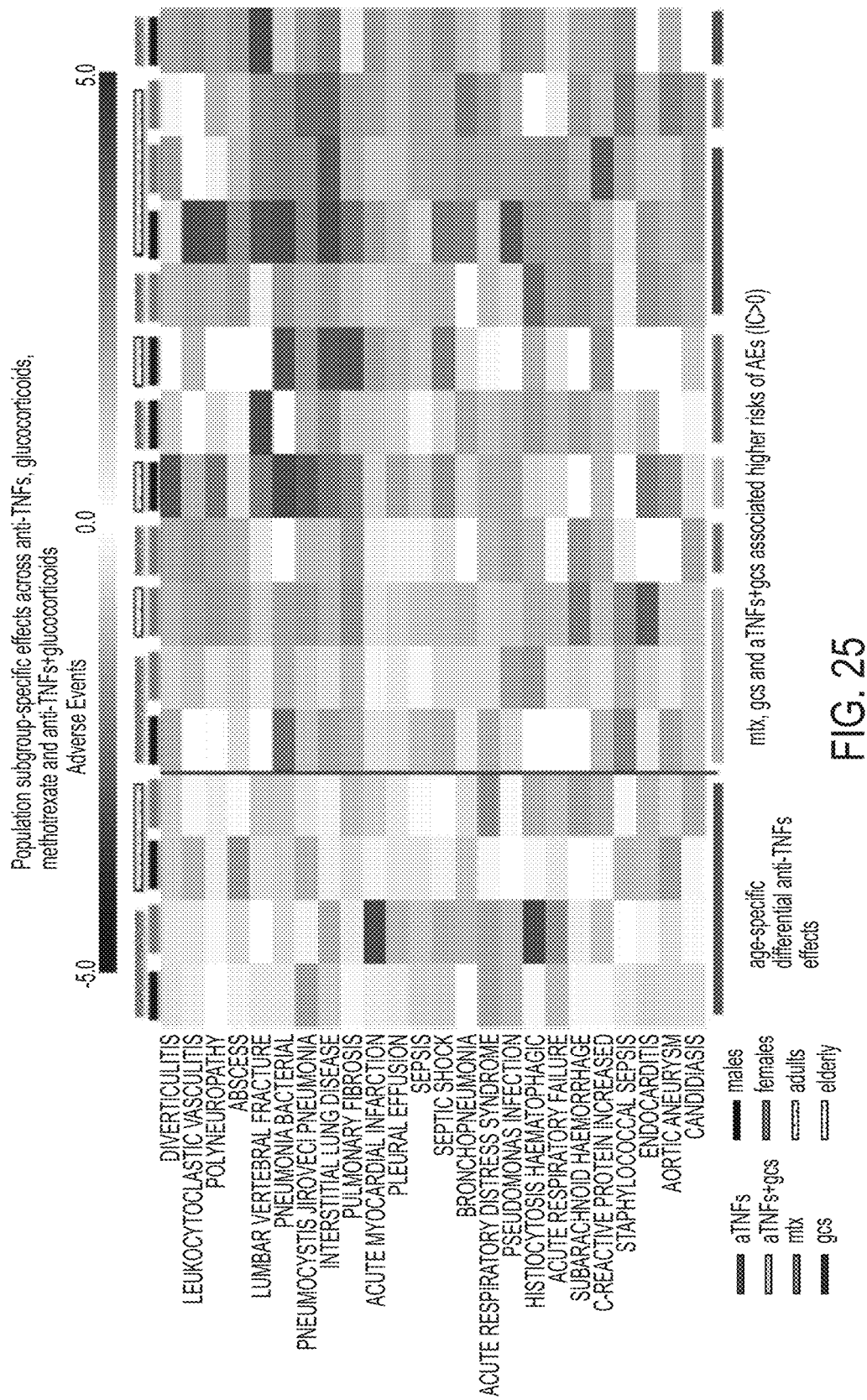
FIG. 25 is a heat map illustrating population subgroup-specific differential responses to therapeutics in TNF-elevated immunoinflammatory disorders.
Figure 27:
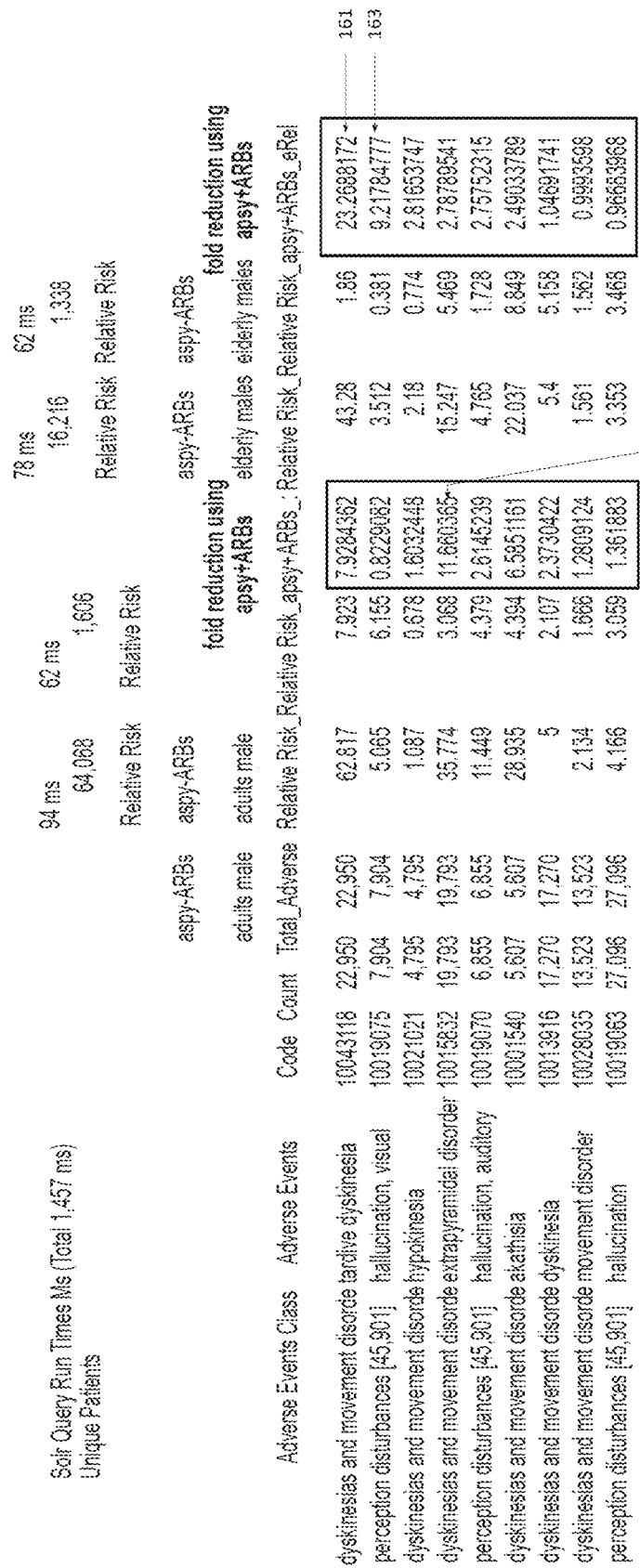
FIG. 27 provides another portion of a results output tending to show promising results when angiotensin receptor blockers are added to the therapeutic regimen of patients on antipsychotics.

As shown in FIG. 16 or 17, the map output may be in the form of a heat map, in which values associated with a relatively higher risk for an adverse event occurring are indicated with the red color 150, while values associated with a relatively lower risk for an adverse event occurring are indicated with a blue color 152. The shade of each color may darken or lighten in accordance with the magnitude of each value. The mapping engine 30 may also be configured to identify and highlight cells or groups of cells as underrepresented 154 (cells or groups tending to show relative lower risks of adverse events occurring). FIG. 25 illustrates an example heat map showing differential therapeutic effects among population subgroups.

With this exemplary approach, the current embodiment allows ontology-based aggregations and subgroupings that facilitate high-dimensional analyses and rich segmentations of differential adverse events, both short term and long term, to identify factors that increase and/or decrease adverse event likelihood and severity, including factors such as age, gender, and the underlying indications that reflect active and disordered biological processes which play an important role in the differential responses to drug effects. Since drug interactions and their severity may also be particularly prone to additional context-specific factors, e.g. chronicity of their use, the current embodiment may provide a novel understanding of therapeutic agent-specific effects and identify high-risk demographic subgroups. By partitioning the data matrices, the current embodiment may offer new insights on the inter-correlation between adverse events (both short term and long term) and population subgroups to recognize potential safety signals that allow us to generate testable hypotheses based on risk-altering interactions. For example, the current system may be used to combine biomarkers and other indicators (including as filters and/or subgroups) to find drug combinations that may lead early onset of a potentially unrelated disease, such as Alzheimer's.

Figure 18:
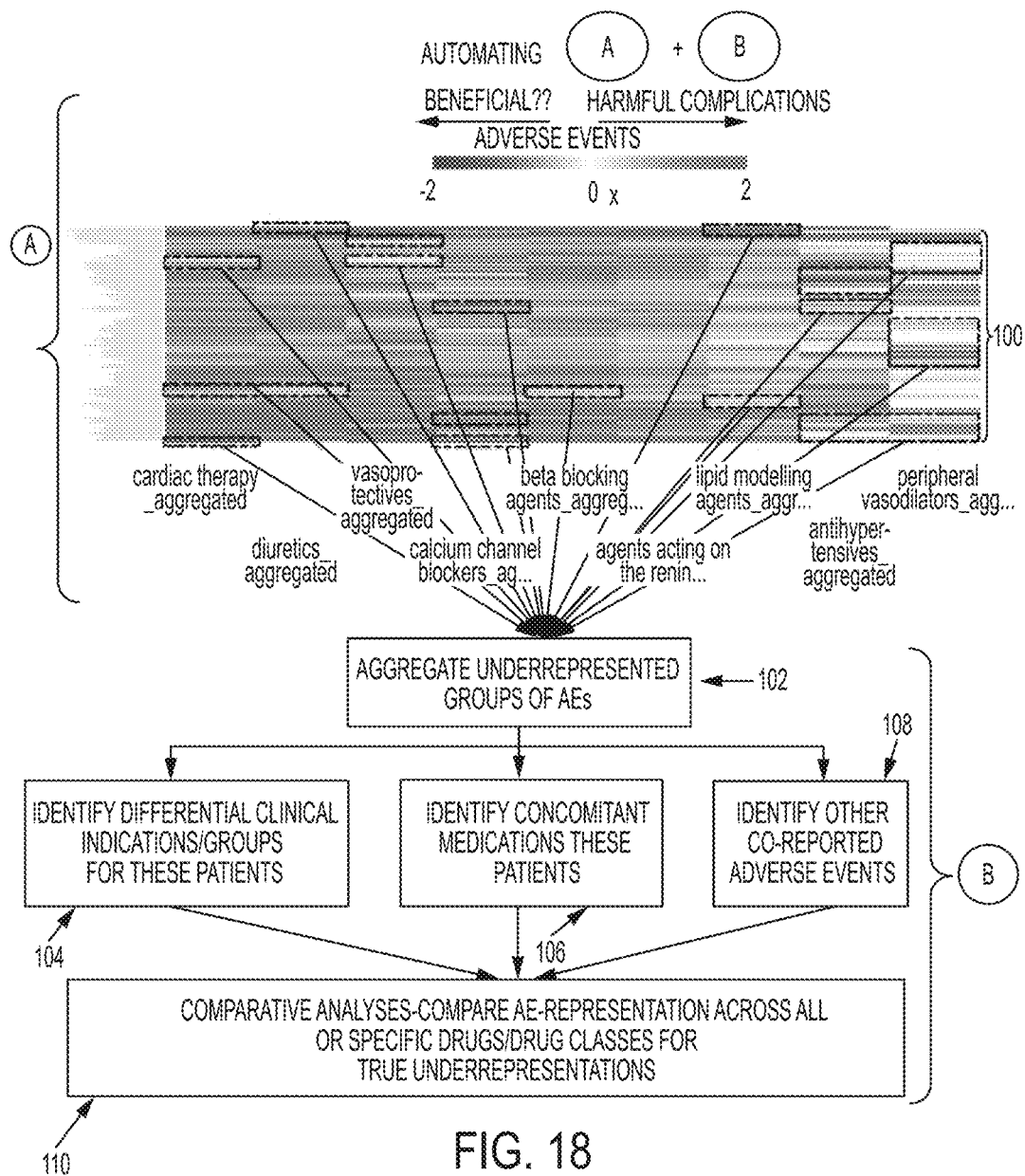
FIG. 18 illustrates a process that a mapping engine may undertake to aggregate underrepresented groups of adverse events; identify differential clinical indications/groups for the patients, identify concomitant medications for the patients, and/or identify other co-reported adverse events; and perform a comparative analysis.

Referring to FIG. 18, the mapping engine 30 may be further configured to process the map 100 to aggregate underrepresented groups of adverse events 102. From the aggregate group(s), the mapping engine 30 may identify differential clinical indications/groups for these patients 104, concomitant medications for these patients 106, and/or other co-reported adverse events 108. From these observations, the mapping engine 30 may perform a comparative analysis 110 to compare adverse event representation across all or specific drugs/drug-classes for a determination of true underrepresentations.

Figure 19:
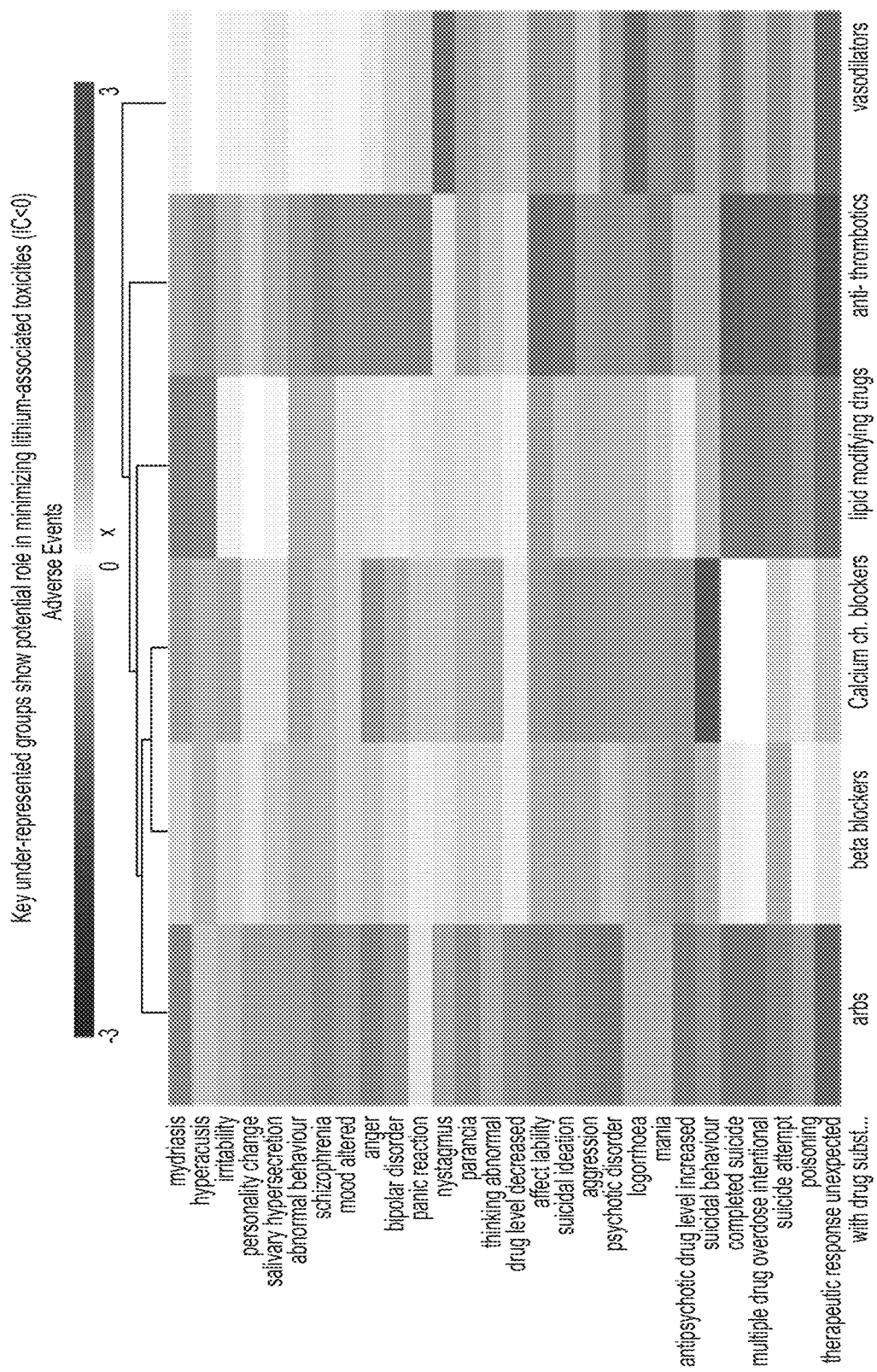
FIG. 19 provides a possible mapping output from a comparative analysis undertaking by a mapping engine.

FIG. 19 provides a possible mapping output from such a comparative analysis, and will be described in further detail below.

FIG. 20 provides another example output from the mapping engine 30, which is in the form of a drug recommendation table for a particular combination of mapped factors. For example, this type of analysis can be used to find the group of drug combinations that have the lowest risk of adverse effects and/or long term adverse effects. The drug recommendation table is based on sub-cohort based iterative analyses within AERSMine that facilitate the identification of known and causal interactions given the patient's current medication and suggesting alternative therapies that a) are more efficacious, b) minimize the interaction effects—the combinatorial strategy increases the benefit to risk ratio, c) based on patient's profile, allow a choice of novel therapeutic alternatives that could minimize specific adverse events or a group of adverse events commonly associated with the primary therapy. The example map shown in FIG. 20 is created by extracting IC values from a subsection of the heat map 100.

Referring to FIG. 21, the relative risk 'RR' value may be calculated for each cell based upon the equation, $$RR = \frac{\left(\frac{a}{a+b}\right)}{\left(\frac{c}{c+d}\right)}$$

where 'a' corresponds to the number of records in the database found by the database mining engine in which the drug identification from the corresponding pair of cohort entries is present and the adverse effects and clinical indications entry from the corresponding pair of cohort entries is also present; where 'b' corresponds to the number of records in the database found by the database mining engine in which the drug identification from the corresponding pair of cohort entries is present and the adverse effects and clinical indications entry from the corresponding pair of cohort entries is not present; where 'c' corresponds to the number of records in the database found by the database mining engine in which the drug identification from the corresponding pair of cohort entries is not present and the adverse effects and clinical indications entry from the corresponding pair of cohort entries is present; and where 'd' corresponds to the number of records in the database found by the database mining engine in which the drug identification from the corresponding pair of cohort entries is not present and the adverse effects and clinical indications entry from the corresponding pair of cohort entries is also not present.

In such a system, the mapping engine may be configured to provide the following visual indications to the cell based upon the calculated relative risk value 'RR': a first visual indication corresponding to a minimal risk if RR is calculated to be less than or equal to 1 (e.g., a blue color shade); a second visual indication corresponding to a moderate risk if RR is calculated to be greater than 1 and less than or equal to 2 (e.g., a lighter shade of red); and a third visual indication corresponding to a high risk if RR is calculated to be greater than 2 (e.g., a darker shade of red).

The RR values are always greater than or equal to 0. The general interpretation of the RR values is RR<=1: Negligible or minimal risk
RR<=2: Moderate Risk
RR>2: High Risk However, this gradation is subjective is used only for guidance. Since RR is a comparative measure, an RR=1.5 tells us that there is 1.5 fold increase in risk, whereas RR=0.5 indicates a 50% reduction in risk. Depending on the nature of a study, RR=1.5 may be high risk.

Referring to FIG. 22, the normalized risk value Information Component ("IC") may be calculated for each cell based upon the equation, $$IC = \log_2((AE\_Count*T)/(Unique\_Patients*AE\_Total))$$

where 'T' corresponds to the total number of records in the database; where 'AE_Count' corresponds the number of records in the database found by the database mining engine in which the drug identification from the corresponding pair of cohort entries is present and the adverse effects and clinical indications entry from the corresponding pair of cohort entries is also present; where 'AE_Total' corresponds the number of records in the database found by the database mining engine in which the adverse effects and clinical indications entry from the corresponding pair of cohort entries is present; and where Unique_Patients corresponds the number of records in the database found by the database mining engine in which the drug identification from the corresponding pair of cohort entries is present.

In such a system the mapping engine 30 may be configured to provide the following visual indications to the cell based upon the calculated IC: a first visual indication corresponding to drug-events database records being less than expected if IC is calculated to be less than 0 (e.g., a blue shade); a second visual indication corresponding to drug-events database records being more than expected if IC is calculated to be greater than 0 (e.g., a red shade); and a third visual indication corresponding to drug-events being as expected if IC is calculated to be equal to 0 (e.g., a clear or white shade).

IC can range between −infinity to +infinity. IC is a safety signal metric and represents the strength of a drug-adverse event pair (IC) across the entire FDA data set. IC is a probabilistic metric—it is based on the principle of observed versus expected number of occurrences. The expected number or occurrences is derived through a probability theory approach. The general interpretation of IC of a drug-adverse event pair is as follows:

IC=0 (observed number of cases is same as expected)
IC<0 (observed number of cases is less than expected)
IC>0 (observed number of cases is higher than expected).

An IC>0 represents a safety signal and presents statistical evidence that may highlight a drug-adverse pair for further clinical review.

A drug-drug-event interaction value 'Ω' for each cell may be calculated from the following equation, $$\Omega = \log 2((n_{111} + alpha)/(E_{111} + alpha));$$

where '$n_{111}$' corresponds to the actual occurrences of the drug-drug-event interaction returned by the mapping engine 30; where '$E_{111}$' corresponds to expected occurrences of the drug-drug-event interaction; and where 'alpha' corresponds to a tuning parameter. In such a system the mapping engine 30 may be configured to provide the following visual indications to the cell based upon the calculated drug-drug-event interaction value Ω: a first visual indication corresponding to drug-drug-events being less than expected if Ω is calculated to be less than 0 (e.g., a blue color shade); a second visual indication corresponding to drug-drug-events being more than expected if Ω is calculated to be greater than 0 (e.g., a red color shade); and a third visual indication corresponding to drug-drug-events being as expected if Ω is calculated to be equal to 0 (e.g. a white or clear color shade). Ω is a safety signal metric useful for representing drug-drug-event conditions, while IC is a safety signal metric useful for representing drug-event conditions.

More specifically, Omega (Ω) is used to identify drug-drug interactions. For example, there is an AND in the query—such as acetaminophen (D1) AND ibuprofen (D2) or two sets. The representation used when calculating Ω is as follows:

Representation: $n_{(D1)\ (D2)\ (adverse\ event)}$ where 1=present and 0=not present.

For example, $n_{001}$ represents the presence of neither D1 nor D2, but the adverse event is reported. Those skilled in the art may utilize the following parameters and algorithm to calculate omega.

% Set required parameters to calculate Omega
$n_{00}$=% All drugs no D1 or D2
$n_{10}$=% Only D1 not D2
$n_{01}$=% Only D2 not D1
$n_{11}$=% D1 and D2 both reported by the patient
% Define tuning parameter alpha
alpha=0.5;
% Calculating the Occurrences of adverse events
$n_{001}$=% no. of adverse events with no D1 or D2
$n_{101}$=% no. of adverse events with only D1 not D2
$n_{011}$=% no. of adverse events with only D2 not D1
$n_{111}$=% no. of adverse events with both D1 and D2
% Relative Reporting Frequencies $$f_{00} = n001/n00;$$

$$f_{10} = n101/n10;$$

$$f_{01} = n011/n01;$$

$$f_{11} = n111/n11;$$

% Calculating the estimator $g_{11}$
% Sample variables initialized to simplify equations $$a = f_{00}/(1-f_{00});$$

$$b = f_{10}/(1-f_{10});$$

$$c = f_{01}/(1-f_{01});$$

if ($f_{10} < f_{00}$)

$$g_{11} = \max(f_{00}, f_{01});$$

elseif ($f_{01} < f_{00}$)

$$g_{11} = \max(f_{00}, f_{10});$$

else $$g_{11} = 1 - (1/(\max(a,b) + \max(a,c) - a + 1));$$

end
% Calculating Omega_zero $$\Omega 0 = \log_2(f_{11}/g_{11});$$

% Calculating the expected occurrences $$E_{111} = g_{11} * n_{11};$$

% Calculating Omega $\Omega = \log_2((n_{111}+\text{alpha})/(E_{111}+\text{alpha}));$ % Calculating the lower bound of the 95% CI $\Omega 025 = \Omega - 3.3*(n_{111}+\text{alpha})^{\wedge}(-\frac{1}{2}) - 2*(n_{111}+\text{alpha})^{\wedge}-(\frac{3}{2});$ Omega can range between −infinity to +infinity. It is a safety signal metric and represents the strength of a drug-drug-adverse event triplet (Omega) across the entire FDA data set. Omega is a probabilistic metric; it is based on the principle of observed versus expected number of occurrences. The expected number or occurrences is derived through a probability theory approach. The general interpretation Omega is as follows:

Omega=0 (observed number of cases are same as expected)

Omega<0 (observed number of cases are less than expected)

Omega>0 (observed number of cases are higher than expected).

Omega>0 represents a safety signal and may present statistical evidence for further clinical review. It suggests that a drug combination is causing an adverse event more frequently than a baseline model.

FIGS. 23A and 23B show a Relative Risk figure. This map provides a sample demonstration of mutually exclusive differential risks across ACE inhibitors, ARBs, and diuretics and shows age and indications-specific responses to drugs. The rich sub-population based analysis identifies and/or captures deeply hidden patterns in large volumes of data that are only evident via an integrated approach using normalizations, ontology aggregations, and stratifications facilitating high-resolution research. This is just one example of how the system of the present disclosure presents a technical solution to the technical problem of making sense of the voluminous FAERS data. Further, the system of the present disclosure enables researchers to identify potential drug-adverse effect interactions and drug-drug interactions that are not intuitive and may not otherwise be possible to realize.

The AERSMine-enabled rich data segmentation and pattern analysis approaches perform well to identify known adverse events, that may be mechanistically linked, and drug interactions as well as candidate novel of each. It has been previously demonstrated that multi-group adverse event correlations not only improves our understanding of adverse event patterns across patient genotype-phenotype-demographic subgroups but also has the potential to generate testable hypotheses. The ultimate goals of these analyses are to protect patients by improving therapeutic selections and monitoring strategies in addition to protecting valuable therapeutics by minimizing harmful interaction choices. AERSMine-enabled analyses may trigger novel therapeutic selections and/or monitoring strategies that might otherwise go unrealized.

In an exemplary embodiment, the quantitative safety signals are detected by measuring the disproportionality between the observed and the expected reporting frequency of a drug-adverse event pair (IC) or drug-drug-adverse event triplet ($\Omega$), with a positive score indicating a potential safety concern requiring further review. The higher the score, the more the combination stands out from the background and represents a suspected outlier association within the FAERS data. These quantitative metrics are exploratory analysis tools for recognizing potential pharmacological interactions and the significant associations (outliers) highlighted by IC and $\Omega$ scores and require further validation and review to establish a causal relationship. To identify significant associations within a large result dataset, Analysis Filters allow a user to prune the analysis matrix using a combination of absolute counts, normalized counts per 1000 patients, relative risks, relative risk p values, and quantitative safety signal metrics (IC or $\Omega$). Ranking of the result matrices is done using a combination of risk and incidence frequencies, high incidence/high risk, low incidence/high risk, or high incidence/low risk, and allows capturing and representation of differential effects across multiple cohorts.

The exemplary embodiment, AERSMine, may be a hybrid system that is built with a Java core designed to run within a Java Servlet Container and provide interactive user sessions based upon HTML5. This hybrid architecture enhances parallel processing of multiple sets and allowing data high-dimensional analysis resulting from numerous internal queries. The query-data model leverages from the construction of multi-dimensional ontologies that provide multi-linked nodular indexing for reducing the querying complexity and provide highly optimal query runtimes that efficiently facilitate complex multi-layered analyses.

The exemplary embodiment, AERSSMine, may be programmed in Java with Servlet technologies for the backend while the front end uses HTML5, CSS, and JavaScript in combination with various JavaScript tools such as JQuery and AngularJS to provide an improved user experience. On the server, the ontologies that map the core data are kept memory resident, with persisted states within a MySQL database server and a SOLR server. The memory resident ontologies can be dumped to the local hard drive and reloaded directly to bypass the dynamic reconstruction of the ontologies and their multi-dimensional inheritances.

Some example uses for the systems disclosed herein include, but are not limited to: (a) researchers can identify therapeutic needs where there is a high incidence of adverse events for a particular indication among all treatments; (b) researchers and pharmaceutical companies may use this to discover novel targets by noticing classes of drugs that are less likely to result in an adverse event among the indications that it is used to treat for; (c) pharmaceutical companies may use this to discover new uses for existing drugs by identifying drugs that result in a lower incidence of an adverse event among the indications it is used to treat for; (d) pharmaceutical companies and clinical research organizations may use this for identifying populations for clinical trials by seeing which patient populations are likely to have the worst adverse events for the standard indication; (e) pharmaceutical companies and clinical research organizations may use this for identifying populations for clinical trials by choosing a narrower indication that has a higher need—or to pick an indication that has adverse events that will more likely respond to their therapy; (f) pharmaceutical company sales representatives can use this to illustrate competitive advantages of their drugs over time; (g) clinicians may use this to identify better treatments for their patients; and (h) patients may use this to identify their treatment options.

Example Analyses Using the Exemplary Embodiment

High-resolution analyses play a critical role in identifying unexpectedly high-risk subgroups, latent associations, known adverse events, and drug interactions and may also serve to identify correlated adverse events that may be mechanistically linked. The analyzable data matrices including absolute counts, normalized reports per 1000 patients, relative risks, drug-adverse event and drug-drug-adverse event signals can be readily visualized through canvasXpress graphics (heatmap, correlation plot, tagcloud etc.) and can be exported in tab-separated files for post-hoc analysis. The following paragraphs demonstrate the use of AERSMine as a multiple cohort analyzer to identify safety signals and analyze differential therapeutic risk patterns across population subgroups, and build testable hypotheses using correlated data patterns to recognize harmful interactions and potential drugs that could mitigate the increased risk of pharmacologic agent-associated adverse events. Specifically, this section illustrates the use of AERSMine for novel hypothesis generation via two examples—1) detecting lithium-associated adverse events and identifying potential drug candidates that could minimize lithium-associated toxicities, and 2) role of anti-TNFs and glucocorticoids in the treatment of tumor necrosis factor elevated disorders, their interactions and exacerbation of pulmonary complications.

Example 1: Lithium Toxicity, Known Drug-Interactions, and Novel Drugs that can Potentially Minimize Lithium-Associated Toxicity Low therapeutic index drugs, such as lithium, are known to be widely associated with clinically significant adverse interactions, and the present inventors sought to determine if pharmacologically unrelated agents that differ in mechanism of action and therapeutic category can be used in combination with lithium to mitigate the risks of adverse events resulting from lithium toxicity. A low therapeutic index indicates that a drug possesses a small difference between an effective and lethal dosage and a relatively small increase in the blood levels due to decrease in metabolism or drug excretion can lead to potentially lethal adverse events. Lithium, a mainstay drug in the treatment of bipolar disorder, is a potentially interacting drug with a low therapeutic index, becomes widely distributed in the central nervous system (CNS) and interacts with a number of neurotransmitters and receptors, decreasing norepinephrine release and increasing serotonin synthesis. Nonsteroidal Anti-Inflammatory Drugs (NSAIDs), including selective and non-selective cyclooxygenase (COX-1, COX-2) inhibitors, hydrochlorothiazide and ACE inhibitors are known to increase serum lithium concentrations by inhibiting renal prostaglandin synthesis. The subsequent excretion of lithium is implicated in neurotoxicity and renal complications.

Figure 30:
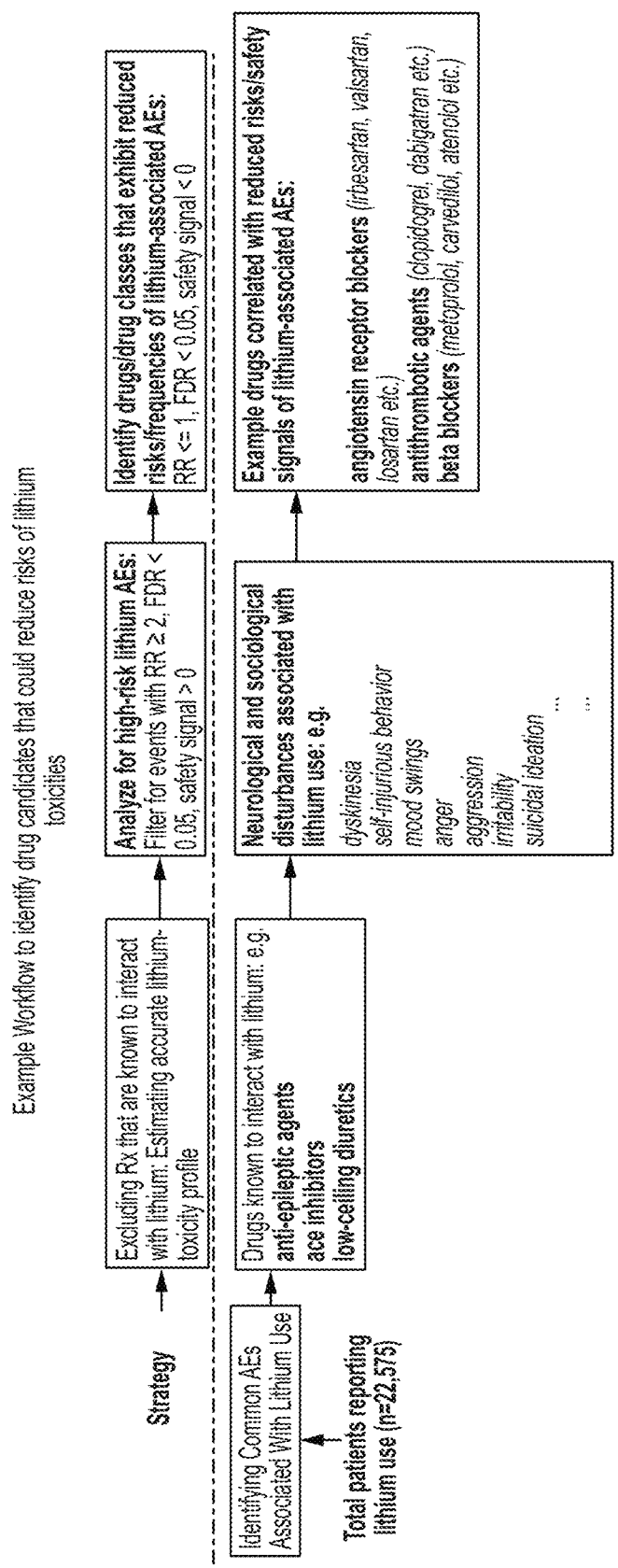
FIG. 30 illustrates an example workflow utilizing the system of the present disclosure to identify drug candidates that may reduce the risks of lithium toxicity.

A simple search on AERSMine shows 22,575 patient reports indicating lithium use in FAERS. Of a total 4,180 adverse events reported by these patients, only 327 adverse events were significantly correlated with lithium use. FIG. 30 illustrates an example workflow showing an AERSMine-facilitated approach to identify drug candidates based on differential lithium toxicities. To establish lithium-adverse event correlation, AERSMine uses multiple quantitative elements such as AE incidence rate, multiple hypothesis testing, relative risk, and safety signals. For this example, the following analytical parameters were used: total reports per adverse event were set to ≥2,000; adverse event and lithium intake co-reported in at least 10 reports; RR set to ≥2; FDR-corrected p-value of <0.001 (Benjamini and Hochberg); and safety signal (i.e., IC) set to >0. Of the resulting set of 327 lithium-correlated adverse events, 57 are known, on-label, lithium-related complications, while the remaining represent potentially novel drug interactions. To better approximate an accurate lithium toxicity profile, AERSMine allows selectively excluding drugs that are known to either interact with lithium or increase serum lithium concentrations such as lamotrigine, carbamazepine, valproic acid, ACE inhibitors, thiazides, coxibs, etc. The integration of ATC ontology allows therapeutic classes such as coxibs, ACE inhibitors etc. to be selectively included or excluded as a class thus utilizing the power of ontological aggregations as integrated within AERSMine.

Figure 31:
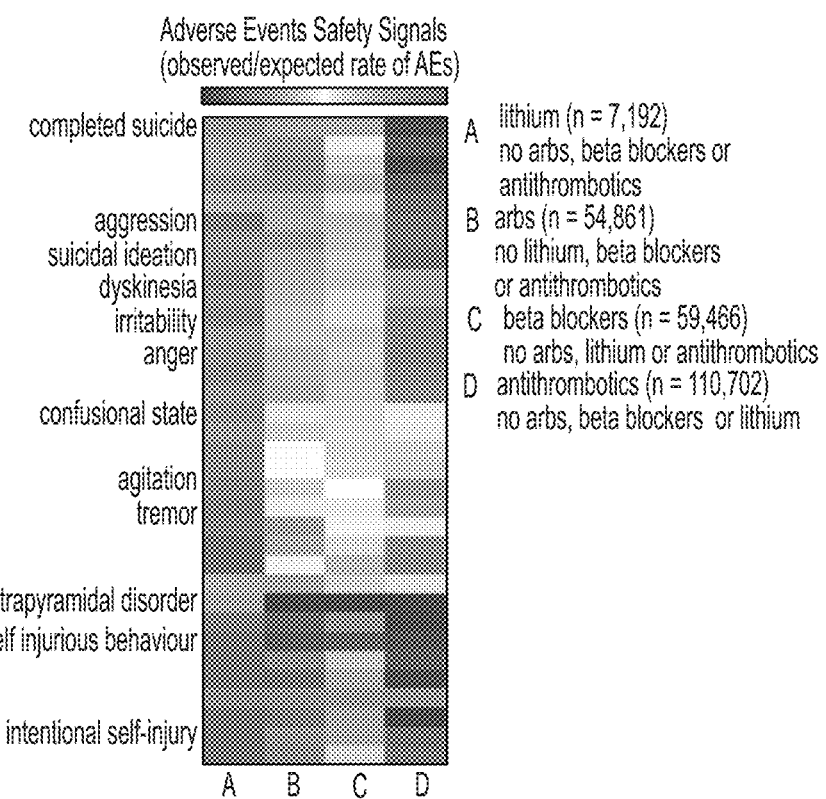
FIG. 31 provides a heat map clustering differential adverse event risks of lithium toxicities as a function of drug class exposures.
Figure 32:
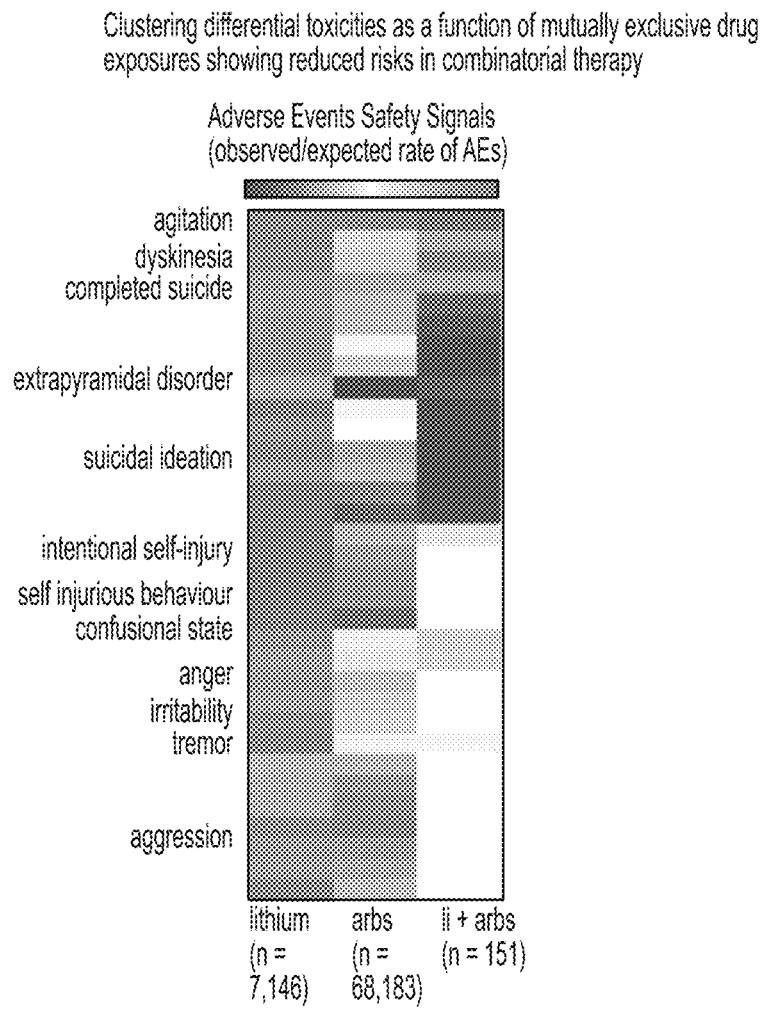
FIG. 32 provides a heat map of a comparative analysis of differential adverse event rates across patients on lithium, angiotensin receptor blockers, and lithium+angiotensin receptor blockers.

Additionally, by excluding patients with comorbidities (e.g., diabetes) reported to worsen mental health and exacerbate neurological symptoms from the analysis, allows AERSMine to accurately represent potentially lithium-specific adverse events (e.g., aggression, irritability, anger, suicidal tendencies, tremors, and other neurological symptoms, movement disorders, personality changes, etc.). The inventors then sought to determine if AERSMine could identify drugs that are inversely correlated with these adverse events, which may indicate a potential reduction in risk and represent a novel combinatorial strategy to mitigate lithium-related toxicity. Using this putative set of lithium-specific neurological adverse events and searching for inversely correlated drugs resulted in a list of drugs, which included losartan, valsartan, warfarin, etc. (no concomitant use with lithium, IC<0, i.e., number of observed events<expected, FDR-corrected p<0.001). To understand how the risks differ across these therapeutic agents, AERSMine additionally allows comparative analyses across multiple drugs or therapeutic classes, which show the differential effects across the inversely correlated drugs. The inventors observed that use of cardiovascular system drugs, specifically angiotensin receptor blocking agents (ARBs), antithrombotic agents, and/or beta blocking agents significantly correlated with reduced risk of lithium-specific neurological adverse effects. FIG. 31 illustrates a clustering of differential adverse event risks of lithium toxicities as a function of drug class exposures to suggest candidate lithium toxicity protective agents. FIG. 32 illustrates a comparative analysis of differential adverse event rates across patients on lithium, ARBs, and lithium+ARBs and shows that the observed reporting rate of neurological adverse events is lower than the expected rate in patients on a combination of lithium and ARBs. For instance, use of ARBs significantly correlated (p<0.001) with decreased risks of anger (RR=0.501) and aggression (RR=0.331), self-injurious behavior (RR=0.14), and suicidal ideation (RR=0.428). A similar safety profile is also seen in cohorts with concomitant use of antithrombotic agents (FIG. 3b, RR≤1, IC<0, p<0.05 Kruskal-Wallis ANOVA). Extending these differential agent-specific effects-based analyses across demographic subgroups, we observed a reduction in the risk of lithium-associated adverse events in both adults and elderly on a cardiovascular system medication. These results suggest that patients on cardiovascular system drugs such as ARBs or antithrombotics could be at lower risks of neurological AEs. The inventors therefore sought to test if concomitant use of lithium and one of the combinatorial drugs presented safety signals suggestive of reduced lithium-specific neurological toxicity. Referring again to FIG. 32, a comparative analysis of differential neurological effects across patients on lithium (n=7,146) or ARBs (n=68, 183) alone, or on the combinatorial lithium and arbs (n=151) indicated that the observed rate of neurological symptoms in the combinatorial cohort is indeed lower than the expected rate ($\Omega$<0, FDR p-value<0.001), suggesting a favorable safety signal profile for the lithium and ARBs combinatorial. The combination of lithium and antithrombotics was not tested because of the insufficient patient numbers for the analysis.

In general, it appears that the mechanism of action of drugs acting on the cardiovascular system may limit the damaging effects of lithium, and the inventors can hypothesize that these drugs could be used to minimize the broad spectrum of lithium-associated toxicities.

Example 2: Anti-TNFs and Glucocorticoids in the Treatment of TNF-Elevated Disorders Exacerbate Pulmonary Complications TNF-elevated clinical indications are characterized by higher levels of pro-inflammatory cytokines, especially TNFα, known for its role in the pathogenesis of autoimmune and inflammatory disorders, host defense mechanisms and initiating response to local injury. However, in excess, TNFα leads to inappropriate inflammation and consequent tissue damage, which may explain the increased probability of tissue injury in patients with autoimmune and immunoinflammatory disorders. Anti-TNF drugs are typically used in the treatment of TNF-elevated disorders, but they are frequently associated with serious adverse effects, necessitating an improved understanding of individual factors that determine efficacy and safety of anti-TNF agents. The inventors used AERSMine to stratify patient subgroups based on anti-TNF-associated adverse events and identify drug combinations that exhibit specifically correlated complications. Through AERSMine, the inventors demonstrated that concomitant use of anti-TNFs with glucocorticoids could potentially lead to significant increases in the risk of adverse events ($p<0.05$), including pulmonary fibrosis, interstitial lung disease, and pulmonary edema.

Figure 24:
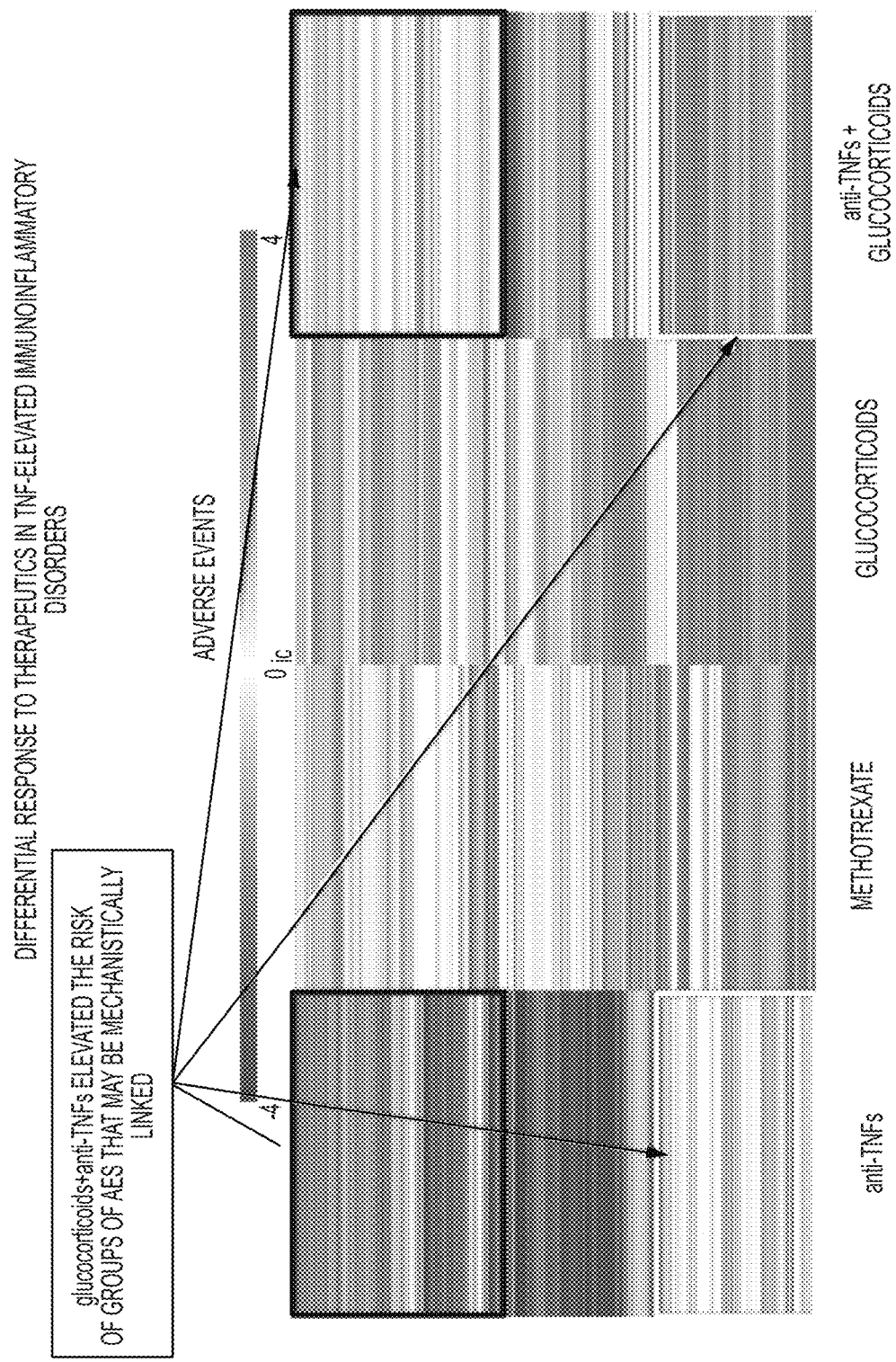
FIG. 24 provides a heat map illustrating differential responses to therapeutics in TNF-elevated immunoinflammatory disorders.
Figure 33:
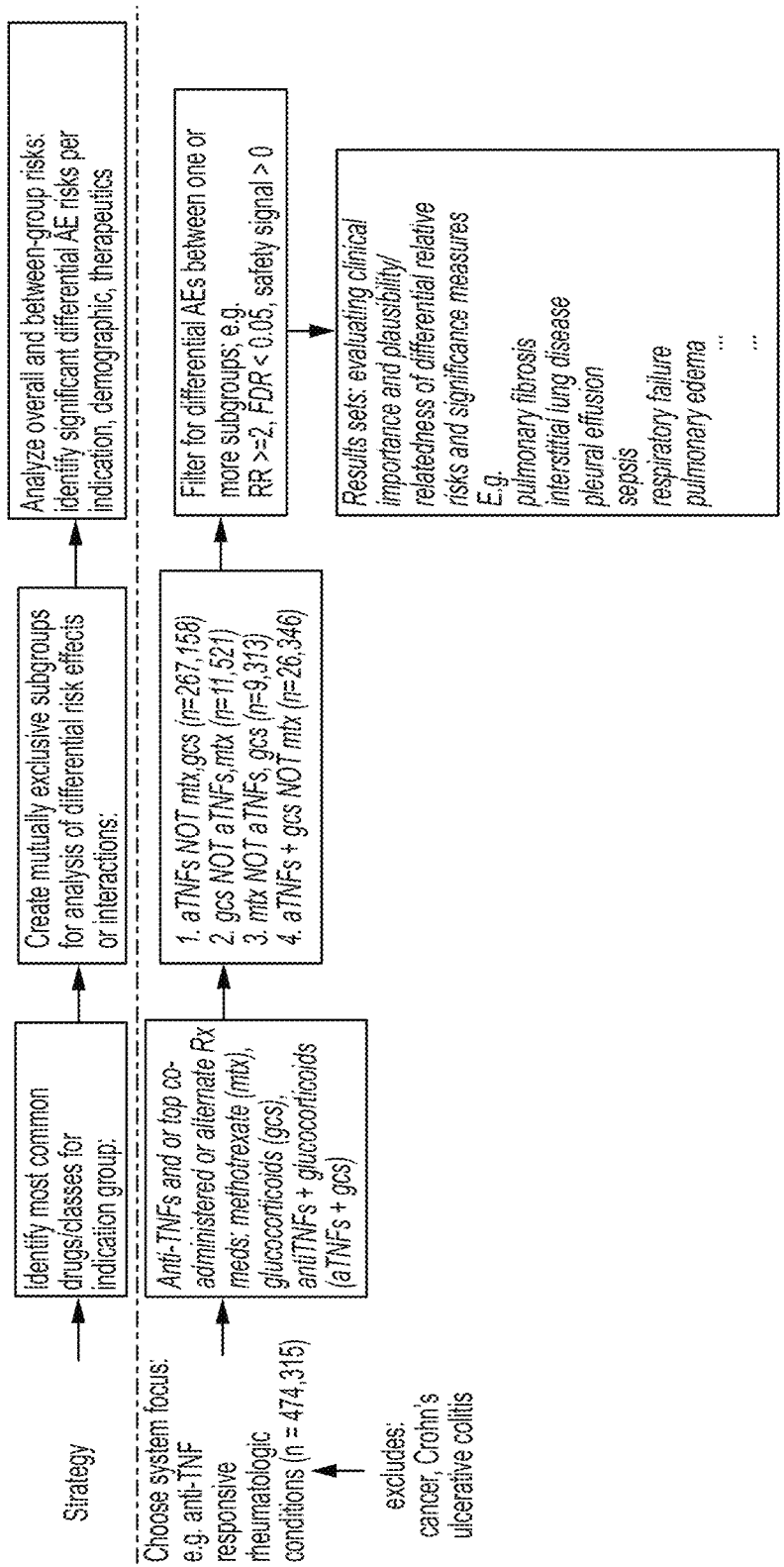
FIG. 33 illustrates an example workflow utilizing the system of the present disclosure to identify modifiers of anti-TNF-associated adverse events.

FIG. 33 illustrates an example workflow of a multidimensional cohort-based study enabled by AERSMine to identify candidate factors with potential to increase/decrease relative risks for anti-TNF-associated adverse events in TNF-elevated disorders. Referring to FIG. 33, the inventors defined four key treatment groups for indications of TNF-responsive inflammatory and autoimmune disorders (rheumatoid arthritis, psoriasis, psoriatic arthropathy, ankylosing spondylitis), excluding any patients with malignancies: aTNFs (anti-TNFs only, n=267,158), gcs (glucocorticoids only, n=11,521), mtx (methotrexate only, n=9,313) and aTNFs+gcs (n=26,346). Defining the four treatment cohorts and analyzing for differential therapy-associated effects across adult and elderly subgroups resulted in a list of 118 adverse events (RR≥2, FDR-corrected p-value<0.001, safety signal>0), including pulmonary edema, fibrosis, interstitial lung disease, pleural effusion, and infections. FIG. 24 provides a heat map representation of differential therapeutic response. The relative risks of developing these adverse events appear to be significantly higher ($p<0.05$, two-tailed Mann-Whitney-Wilcoxon test) in patients on corticosteroids compared to baseline anti-TNFs.

Figure 34:
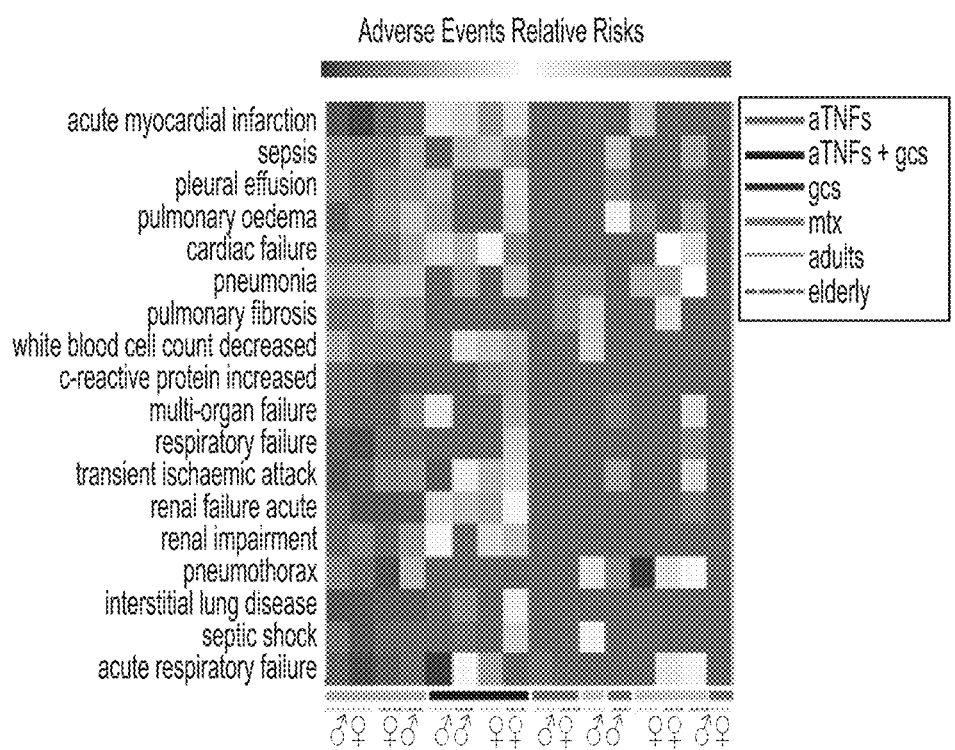
FIG. 34 provides a heat map illustrating differential adverse event risks among population subgroups as a function of indication, demographic, and use of various drugs/drug combinations.

Analyzing for differential effects across the treatment groups shows comparatively lower adverse event occurrence rates in patients on anti-TNFs than those on glucocorticoids or combination of anti-TNFs and glucocorticoids (2.5-fold reduction in reports per 1000 patients). The increased rate of adverse event-occurrence associated with glucocorticoids is particularly important in view of the treatment regimen, which encourages the concomitant use of glucocorticoid therapy until the effects of the TNF-antagonists are clinically observed. Additionally, we observed that patients on combination of anti-TNFs and glucocorticoids are at significantly increased risk (at least 2.5-fold, $p<0.05$, two-tailed Mann-Whitney-Wilcoxon test) of pulmonary fibrosis, interstitial lung disease, sepsis, septic shock, pleural effusion, pulmonary edema, respiratory failure, and pneumonia. Analyzing further for demographic subgroup-specific differential effects also showed increased risks associated with concomitant use of anti-TNFs and glucocorticoids, particularly in the elderly, who are at most risk of life threatening adverse events. FIG. 34 illustrates differential adverse event risks among population subgroups as a function of indication, demographic, and the use of anti-TNFs, glucocorticoids, methotrexate, and combinations suggesting significant elevated risk compared to baseline anti-TNF therapy. The heat map in FIG. 34 shows that concomitant use of glucocorticoids with anti-TNF therapy significantly exacerbated the risk of groups of adverse events ($p≤0.05$, two-tailed Mann-Whitney-Wilcoxon test) in comparison with baseline anti-TNF monotherapy. The risks of interstitial lung disease, pulmonary edema, and fibrosis were elevated in patients on combination of anti-TNFs and glucocorticoids ($p≤0.05$, two-tailed Mann-Whitney-Wilcoxon test).

To improve our understanding about the molecular basis of these adverse events and potential causal mechanisms, we can extend these analyses through systems biology-based integrative approaches that aggregate mouse phenotype data, gene ontology and pathway interaction databases, to suggest modification of anti-TNF-based therapeutic strategies to minimize glucocorticoid-associated combinatorial risk of severe adverse events.

Example 3: Angiotensin Receptor Blockers ("ARBs") to Minimize the Progression of Neurological Disorders In this example, the inventors analyzed 5.9 million patients using AERSMine. The inventors, through AERSMine, were able to realize and visualize the apparent beneficial effect of ARBs on minimizing aggression, irritability, and other mental-related adverse events. This is a heretofore unknown characteristic of ARBs. The inventors hypothesized that ARBs may be particularly useful to patients known to suffer from such mental-related adverse events, such as patients on antipsychotics.

To this end, the inventors utilized AERSMine and selected for patient reports listing both angiotensin receptors and antipsychotics. The results are very promising when ARBs are added to the therapeutic regimen of patients who are on antipsychotics. A sample of results is displayed in FIGS. 26, 27, 28, and 29. The results strongly suggest that ARBs can be used to minimize the progression of mental deterioration, dyskinesias, movement disorders, hallucinations, and other related adverse events. Adding ARBs to antipsychotics appears to show a significant potential in reducing the risk of multiple behavioral and/or neurological outcomes for, e.g., tardive dyskinesia (23-fold reduction 161, p=0.0032 162 in elderly males), visual hallucinations (9-fold reduction 163, p=0.0002 164 in elderly males), extrapyramidal disorder (11.6-fold reduction 165, p=0.0005 166 in adult males), and akathisia (5.6-fold reduction 167, p=0.00005 168 in adult females).

Statistically, using Fisher's exact test, there is a strong significance in the reduction of behavioral and/or neurological risks when ARBs are added to antipsychotics. This promises to have a profound impact in improving longitudinal outcomes. This is a novel observation in the medical, pharmaceutical, and pharmacovigilance fields and may be especially important, as ARBs are well-tolerated and relatively safe drugs.

Computer and Processing Structures

To provide additional context for various aspects of the present invention, such as the database mining and mapping engine(s) 28, 30 and/or the user computer(s) 32, the following discussion is intended to provide a brief, general description of a suitable computing environment in which the various aspects of the invention may be implemented. Those skilled in the art will recognize that the invention also may be implemented in combination with various computer program modules and/or as a combination of hardware and software.

Generally, program modules include routines, programs, components, data structures, etc., that perform particular tasks or implement particular abstract data types. Moreover, those skilled in the art will appreciate that aspects of the inventive methods may be practiced with other computer system configurations, including single-processor or multi-processor computer systems, minicomputers, mainframe computers, as well as personal computers, hand-held wireless computing devices, microprocessor-based or programmable consumer electronics, and the like, each of which can be operatively coupled to one or more associated devices. Aspects of the invention may also be practiced in distributed computing environments where certain tasks are performed by remote processing devices that are linked through a communications network. In a distributed computing environment, program modules may be located in both local and remote memory storage devices.

A computer may include a variety of computer readable media. Computer readable media may be any available media that can be accessed by the computer and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD ROM, digital video disk (DVD) or other optical disk storage, magnetic cassettes, magnetic tape, magnetic disk storage or other magnetic storage devices, or any other medium which may be used to store the desired information and which may be accessed by the computer.

An exemplary environment for implementing various aspects of the invention may include a computer that includes a processing unit, a system memory and a system bus. The system bus couples system components including, but not limited to, the system memory to the processing unit. The processing unit may be any of various commercially available processors. Dual microprocessors and other multi-processor architectures may also be employed as the processing unit.

The system bus may be any of several types of bus structure that may further interconnect to a memory bus (with or without a memory controller), a peripheral bus, and a local bus using any of a variety of commercially available bus architectures. The system memory may include read only memory (ROM) and/or random access memory (RAM). A basic input/output system (BIOS) is stored in a non-volatile memory such as ROM, EPROM, EEPROM, which BIOS contains the basic routines that help to transfer information between elements within the computer, such as during start-up. The RAM may also include a high-speed RAM such as static RAM for caching data.

The computer may further include an internal hard disk drive (HDD) (e.g., EIDE, SATA), which internal hard disk drive may also be configured for external use in a suitable chassis, a magnetic floppy disk drive (FDD), (e.g., to read from or write to a removable diskette) and an optical disk drive, (e.g., reading a CD-ROM disk or, to read from or write to other high capacity optical media such as the DVD). The hard disk drive, magnetic disk drive and optical disk drive may be connected to the system bus by a hard disk drive interface, a magnetic disk drive interface and an optical drive interface, respectively. The interface for external drive implementations includes at least one or both of Universal Serial Bus (USB) and IEEE 1394 interface technologies.

The drives and their associated computer-readable media may provide nonvolatile storage of data, data structures, computer-executable instructions, and so forth. For the computer, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules may be stored in the drives and RAM, including an operating system, one or more application programs, other program modules and program data. All or portions of the operating system, applications, modules, and/or data may also be cached in the RAM. It is appreciated that the invention may be implemented with various commercially available operating systems or combinations of operating systems.

It is within the scope of the disclosure that a user may enter commands and information into the computer through one or more wired/wireless input devices, for example, a touch screen display, a keyboard and/or a pointing device, such as a mouse. Other input devices may include a microphone (functioning in association with appropriate language processing/recognition software as known to those of ordinary skill in the technology), an IR remote control, a joystick, a game pad, a stylus pen, or the like. These and other input devices are often connected to the processing unit through an input device interface that is coupled to the system bus, but may be connected by other interfaces, such as a parallel port, an IEEE 1394 serial port, a game port, a USB port, an IR interface, etc.

A display monitor or other type of display device may also be connected to the system bus via an interface, such as a video adapter. In addition to the monitor, a computer may include other peripheral output devices, such as speakers, printers, etc.

The computer may operate in a networked environment using logical connections via wired and/or wireless communications to one or more remote computers. The remote computer(s) may be a workstation, a server computer, a router, a personal computer, a portable computer, a personal digital assistant, a cellular device, a microprocessor-based entertainment appliance, a peer device or other common network node, and may include many or all of the elements described relative to the computer. The logical connections depicted include wired/wireless connectivity to a local area network (LAN) and/or larger networks, for example, a wide area network (WAN). Such LAN and WAN networking environments are commonplace in offices, and companies, and facilitate enterprise-wide computer networks, such as intranets, all of which may connect to a global communications network such as the Internet.

The computer may be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi (such as IEEE 802.11x (a, b, g, n, etc.)) and Bluetooth™ wireless technologies. Thus, the communication may be a predefined structure as with a conventional network or simply an ad hoc communication between at least two devices.

The system may also include one or more server(s). The server(s) may also be hardware and/or software (e.g., threads, processes, computing devices). The servers may house threads to perform transformations by employing aspects of the invention, for example. One possible communication between a client and a server may be in the form of a data packet adapted to be transmitted between two or more computer processes. The data packet may include a cookie and/or associated contextual information, for example. The system may include a communication framework (e.g., a global communication network such as the Internet) that may be employed to facilitate communications between the client(s) and the server(s).

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A system for transforming cumulative clinical adverse events data into a visual representation for improved understanding of differential clinical outcomes, comprising:
    a pharmacological hierarchical ontology of drug identifications;
    a phenotype hierarchical ontology of clinical adverse effects and clinical indications;
    a clinical record database comprising records containing clinical event information, each record including (a) demographic information for a patient experiencing a clinical event, (b) clinical indication information for the patient experiencing the clinical event, (c) drug identification information associated with the clinical event, (d) adverse reaction information associated with the clinical event, and (e) patient outcome information;
    a database mining engine configured to,
        iteratively progress through at least a selected portion of each of the pharmacological hierarchical ontology and the phenotype hierarchical ontology to iteratively select respective pairs of cohort entries from each of the pharmacological hierarchical ontology and the phenotype hierarchical ontology, and
        for each pair of cohort entries, query the clinical record database for the database records matching the items in the pair of cohort entries; and
    a mapping engine configured to,
        map each pair of cohort entries into a data matrix comprising a cell for each pair of cohort entries,
        apply a value associated with a drug-drug-event interaction to each cell which is, at least in part a function of a number of expected occurrences of the drug-drug-event interaction and a number of actual occurrences of the drug-drug-event interaction returned by the mapping engine, and
        provide a visual representation of the data matrix including each mapped pair of cohort entries and each applied value.

2. The system of claim 1, wherein the mapping engine is configured to apply a normalized per "x" number of patients value to each cell corresponding to a number of drug-event records returned by the database mining engine.

3. The system of claim 1, wherein the mapping engine is configured to apply a relative risk value to each cell, wherein the relative risk value pertains, at least in part, to the relative risk of the adverse effects and clinical indications entry from the corresponding pair of cohort entries being associated with the drug identification from the corresponding pair of cohort entries.

4. The system of claim 3, wherein the mapping engine is configured to calculate the relative risk value 'RR' to each cell based upon the equation $$RR = \frac{\left(\frac{a}{a+b}\right)}{\left(\frac{c}{c+d}\right)}$$

where 'a' corresponds to the number of records in the database found by the database mining engine in which the drug identification from the corresponding pair of cohort entries is present and the adverse effects and clinical indications entry from the corresponding pair of cohort entries is also present;
    where 'b' corresponds to the number of records in the database found by the database mining engine in which the drug identification from the corresponding pair of cohort entries is present and the adverse effects and clinical indications entry from the corresponding pair of cohort entries is not present;
    where 'c' corresponds to the number of records in the database found by the database mining engine in which the drug identification from the corresponding pair of cohort entries is not present and the adverse effects and clinical indications entry from the corresponding pair of cohort entries is present; and
    where 'd' corresponds to the number of records in the database found by the database mining engine in which the drug identification from the corresponding pair of cohort entries is not present and the adverse effects and clinical indications entry from the corresponding pair of cohort entries is also not present.

5. The system of claim 4, wherein providing the visual representation includes applying the following visual indications to the cell based upon the calculated relative risk value 'RR':
    a first visual indication corresponding to a minimal risk if RR is calculated to be less than or equal to 1;
    a second visual indication corresponding to a moderate risk if RR is calculated to be greater than 1 and less than or equal to 2; and
    a third visual indication corresponding to a high risk if RR is calculated to be greater than 2.

6. The system of claim 1, wherein the mapping engine is configured to apply a normalized risk value to each cell, wherein the normalized risk value pertains, at least in part, to the relative risk of the adverse effects and clinical indications entry from the corresponding pair of cohort entries being associated with the drug identification from the corresponding pair of cohort entries.

7. The system of claim 6, wherein the mapping engine is configured to calculate the normalized risk value 'IC' to each cell based upon the equation, IC=log 2((AE Count*$T$)/(Unique Patients*AE Total))

where 'T' corresponds to the total number of records in the database;

where 'AE Count' corresponds the number of records in the database found by the database mining engine in which the drug identification from the corresponding pair of cohort entries is present and the adverse effects and clinical indications entry from the corresponding pair of cohort entries is also present;

where 'AE Total' corresponds the number of records in the database found by the database mining engine in which the adverse effects and clinical indications entry from the corresponding pair of cohort entries is present; and where Unique Patients corresponds the number of records in the database found by the database mining engine in which the drug identification from the corresponding pair of cohort entries is present.

8. The system of claim 7, wherein providing the visual representation includes applying the following visual indications to the cell based upon the calculated normalized risk value 'IC':

a first visual indication corresponding to drug-events database records being less than expected if IC is calculated to be less than 0;

a second visual indication corresponding to drug-events database records being more than expected if IC is calculated to be greater than 0;

a third visual indication corresponding to drug-events being as expected if IC is calculated to be equal to 0.

9. The system of claim 1, wherein the configured to apply providing the visual representation includes applying a color to the cell representing the applied value for the cell.

10. The system of claim 9, wherein a first color corresponds to risk of the adverse effects and clinical indications entry from the corresponding pair of cohort entries being associated with the drug identification from the corresponding pair of cohort entries being relatively low; and a second color corresponds to risk of the adverse effects and clinical indications entry from the corresponding pair of cohort entries being associated with the drug identification from the corresponding pair of cohort entries being relatively high.

11. The system of claim 1, wherein:

the database mining engine is configured to, iteratively progress through at least the selected portion of each of the pharmacological hierarchical ontology and the phenotype hierarchical ontology to iteratively select respective sets of cohort entries, each set including at least a first and second entry from the pharmacological hierarchical ontology and each set including at least an entry from the phenotype hierarchical ontology, and for each set of cohort entries, query the clinical record database for the database records matching the items in the set of cohort entries; and the mapping engine configured to, map each set of cohort entries into a data matrix comprising a cell for each set of cohort entries, and apply the drug-drug-event interaction value to each cell which is, at least in part a function of the number of database records matching a number of items returned by the database mining engine for the corresponding cohort entries.

12. The system of claim 11, wherein the drug-drug-event interaction value applied to each cell is 'Ω' and 'Ω' is calculated from the following equation, Ω=log 2(($n$111+alpha)/($E$111+alpha));

where 'n111' corresponds to the number of actual occurrences of the drug-drug-event interaction returned by the mapping engine;

where 'E111' corresponds to the number of expected occurrences of the drug-drug-event interaction; and where 'alpha' corresponds to a tuning parameter.

13. The system of claim 12, wherein providing the visual representation includes applying the following visual indications to the cell based upon the calculated drug-drug-event interaction value 'Ω':

a first visual indication corresponding to drug-drug-events being less than expected if Ω is calculated to be less than 0;

a second visual indication corresponding to drug-drug-events being more than expected if Ω is calculated to be greater than 0;

a third visual indication corresponding to drug-drug-events being as expected if Ω is calculated to be equal to 0.

14. The system of claim 1, wherein providing the visual representation includes applying a color to the cell representing the applied value for the cell.

15. The system of claim 1, wherein the database mining engine is configured to a selected subgroup of at least one of the pharmacological hierarchy and the phenotype hierarchy.

16. The system of claim 15, wherein the subgroup pertains to criteria for at least one field in the clinical record database.

17. The system of claim 15, wherein the subgroup pertains to at least one demographic criteria in the clinical record database.

18. The system of claim 15, wherein the subgroup pertains to at least one clinical information criteria in the clinical record database.

19. The system of claim 15, wherein the subgroup pertains to at least one drug identification criteria in the clinical record database.

20. The system of claim 15, wherein the subgroup pertains to at least one adverse reaction criteria in the clinical record database.

21. The system of claim 15, wherein the subgroup pertains to at least one patient outcome criteria in the clinical record database.

22. The system of claim 15, wherein the subgroup pertains to two more of at least one demographic criteria, at least one clinical information criteria, at least one drug identification criteria, at least one adverse reaction criteria and at least one patient outcome criteria.

23. The system of claim 15, wherein the mapping engine is configured to display a comparison of values in the cells associated with the subgroup versus cells associated with a global representation of the database records.

24. The system of claim 1, wherein the pharmacological hierarchical ontology of drug identifications is ordered under a multitude of parent concepts, and a multitude of generic pharmacological concepts under the parent concepts.

25. The system of claim 1, wherein the drug identifications in the pharmacological hierarchical ontology include a plurality of drug entries, wherein each drug entry includes a plurality of names taken from a group consisting of: clinical names for the drug, commercial brand names for the drug, molecular names for the drug, foreign names for the drug, spelling variants for the drug, and mis-spellings for the drug.

26. The system of claim 1, wherein the phenotype hierarchical ontology of clinical adverse effects and clinical indications is ordered under a multitude of hierarchical MedRA concepts.

27. The system of claim 1, wherein the visual representation is provided in at least one of the following visual formats:
 a heat map;
 bar chart;
 circular plot;
 a correlation plot; and
 a tag cloud.

28. The system of claim 1, wherein providing the visual representation includes specifically highlighting those of the plurality of cells that show at least one of under-represented adverse reaction information and over-represented adverse reaction information.

29. The system of claim 1, wherein providing the visual representation includes producing the plurality of cells in the form of an output that can be displayed on a user's computer.

30. A system for mining cumulative clinical adverse events data for improved understanding of differential clinical outcomes, comprising:
 a pharmacological hierarchical ontology of drug identifications;
 a phenotype hierarchical ontology of clinical adverse effects and clinical indications;
 a clinical record database comprising records containing clinical event information, each record including (a) clinical indication information for the patient experiencing the clinical event, (b) drug identification information associated with the clinical event, and (c) adverse reaction information associated with the clinical event;
 a database mining engine configured to (i) iteratively progress through at least a selected portion of each of the pharmacological hierarchical ontology and the phenotype hierarchical ontology to iteratively select respective pairs of cohort entries from each of the pharmacological hierarchical ontology and the phenotype hierarchical ontology, and (ii) for each pair of cohort entries, query the clinical record database for the database records matching the items in the pair of cohort entries; and
 a mapping engine configured to (i) map each pair of cohort entries into a data matrix comprising a cell for each pair of cohort entries, (ii) apply a first value associated with a drug-drug-event interaction to each cell which is, at least in part a function of a number of expected occurrences of the drug-drug-event interaction and a number of actual occurrences of the drug-drug-event interaction returned by the mapping engine, and (iii) provide a visual representation of the data matrix including each mapped pair of cohort entries and each applied first value.

31. The system of claim 30, wherein the mapping engine is configured to apply a second value to each cell which is, at least in part a function of the number of drug-event database records matching a number of items returned by the database mining engine for the corresponding cohort entries.

32. The system of claim 30, wherein the clinical record database further includes (d) and (e) patient outcome information.

* * * * *